United States Patent
Solaiman et al.

(10) Patent No.: US 10,190,144 B2
(45) Date of Patent: Jan. 29, 2019

(54) **PRODUCTION OF DIRHAMNOSE-LIPID IN RECOMBINANT NONPATHOGENIC BACTERIUM *PSEUDOMONAS CHLORORAPHIS***

(71) Applicant: THE UNITED STATES OF AMERICA, AS REPRESENTED BY THE SECRETARY OF AGRICULTURE, Washington, DC (US)

(72) Inventors: Daniel Solaiman, Dresher, PA (US); Richard D. Ashby, Glenside, PA (US); Jonathan A. Zerkowski, Wayne, PA (US); Nereus W. Gunther, Wyndmoor, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 170 days.

(21) Appl. No.: 14/892,793

(22) PCT Filed: Jun. 3, 2014

(86) PCT No.: PCT/US2014/040652
§ 371 (c)(1),
(2) Date: Nov. 20, 2015

(87) PCT Pub. No.: WO2014/197457
PCT Pub. Date: Dec. 11, 2014

(65) Prior Publication Data
US 2016/0102330 A1    Apr. 14, 2016

Related U.S. Application Data

(60) Provisional application No. 61/831,776, filed on Jun. 6, 2013.

(51) Int. Cl.
| | | |
|---|---|---|
| *C12P 19/44* | (2006.01) | |
| *C12P 7/64* | (2006.01) | |
| *C07K 14/21* | (2006.01) | |
| *C12N 9/10* | (2006.01) | |
| *C12P 19/18* | (2006.01) | |
| *C12N 15/64* | (2006.01) | |
| *C12N 15/52* | (2006.01) | |

(52) U.S. Cl.
CPC ............ *C12P 19/44* (2013.01); *C07K 14/21* (2013.01); *C12N 9/1051* (2013.01); *C12N 15/52* (2013.01); *C12N 15/64* (2013.01); *C12P 7/64* (2013.01); *C12P 7/6409* (2013.01); *C12P 19/18* (2013.01); *C12Y 204/01* (2013.01)

(58) Field of Classification Search
None
See application file for complete search history.

(56) References Cited

U.S. PATENT DOCUMENTS

| | | |
|---|---|---|
| 5,767,090 A | 6/1998 | Stanghellini et al. |
| 7,202,063 B1 | 4/2007 | Gunther et al. |
| 2007/0191292 A1 | 8/2007 | Gandhi et al. |
| 2013/0130319 A1 | 5/2013 | Schaffer et al. |

FOREIGN PATENT DOCUMENTS

| | | |
|---|---|---|
| EP | 2573 172 A1 | 3/2013 |
| EP | 2573172 A1 | 3/2013 |

OTHER PUBLICATIONS

Roy, Paul H. et al., "Complete genome sequence of the multiresistant taxonomic outlier Pseudomnas aeruginosa PA7", PLoS One, vol. 5, No. 1, pp. e8842, Jan. 22, 2010.
Abdel-Mawgoud et al., "Rhamnolipids: diversity of structures, microbial origins and roles", (2010) Appl Microbiol Biotechnol 86:1323-1336.
Cabrera-Valladares et al., "Monorhamnolipids and 3-(3-hydroxyalkanoyloxy) alkanoic acids (HAAs) production using *Escherichia coli* as a heterologous host", (2006) Appl Microbiol Biotechnol 73:187-197.
Campos-Garcia et al., "The Pseudomonas aeruginosa rhlG Gene Encodes an NADPH-Dependent β-Ketoacyl Reductase Which Is Specifically Involved in Rhamnolipid Synthesis", (1998) Journal of Bacteriology 180(17): 4442-4451.
Cha et al., "Heterologous production of Pseudomonas aeruginosa EMS1 biosurfactant in Pseudomonas putida", (2008) Bioresource Technology 99: 2192-2199.
De'Ziel et al., "rhlA is required for the production of a novel biosurfactant promoting swarming motility in Pseudomonas aeruginosa: 3-(3-hydroxyalkanoyloxy)alkanoic acids (HAAs), the precursors of rhamnolipids", (2003) Microbiology 149:2005-2013.
Gunther IV et al., "Production of Rhamnolipids by *Pseudomonas chlororaphis*, a Nonpathogenic Bacterium", (2005) Applied and Environmenttal Microbiology 71(5): 2288-2293.
Miller et al., "Structure of RhlG, an Essential β-Ketoacyl Reductase in the Rhamnolipid Biosynthetic Pathway of Pseudomonas aeruginosa*", (2006) The Journal of Biological Chemistry 281(26): 18025-18032.

(Continued)

*Primary Examiner* — Suzanne M Noakes
*Assistant Examiner* — Jae W Lee
(74) *Attorney, Agent, or Firm* — David L. Marks; John D. Fado; Gail E. Poulos

(57) ABSTRACT

*Pseudomonas chlororaphis* NRRL B-30761 produces monorhamnolipids with predominantly 3-hydroxydodecenoyl-3-hydroxydecanoate ($C_{12:1}$-$C_{10}$) or 3-hydroxydodecanoyl-3-hydroxydecanoate ($C_{12}$-$C_{10}$) as the lipid moiety under static growth conditions. The cloning and sequencing of three genes and proteins involved in the biosynthesis of monorhamnose-lipid ($R_1L$) is described. Expression of two of these genes, i.e., rhlA and rhlB, together in *P. chlororaphis* NRRL B-30761 increases $R_1L$ production by at least 10-fold. Also the generation of a recombinant *P. chlororaphis* NRRL B-30761 capable of synthesizing dirhamnose-lipid ($R_2L$) is described. Characterization of $R_1L$ and $R_2L$ produced by the recombinant *P. chlororaphis* NRRL B-30761 is also described.

9 Claims, 8 Drawing Sheets
Specification includes a Sequence Listing.

(56) References Cited

OTHER PUBLICATIONS

Müller et al., "Evaluation of rhamnolipid production capacity of Pseudomonas aeruginosa PAO1 in comparison to the rhamnolipid over-producer strains DSM 7108 and DSM 2874", (2011) Appl Microbiol Biotechnol 89:585-592.

Nguyen et al., "Characterization and Emulsification Properties of Rhamnolipid and Sophorolipid Biosurfactants and Their Applications", (2011) Int. Journal of Molecular Sciences 12:1232-1244.

Ochsner et al., "Production of Pseudomonas aeruginosa Rhamnolipid Biosurfactants in Heterologous Hosts", (1995) Applied and Environmental Microbiology 61(9): 3503-3506.

Roy et al., "Complete Genome Sequence of the Multiresistant Taxonomic Outlier Pseudomonas aeruginosa PA7", (2010) PLOSOne 5(1): e8842, 11 pages.

Singh et al., "Rhamnolipids Production by Multi-metal-Resistant and Plant-Growth-Promoting Rhizobacteria", (2013) Applied Biochem Biotechnol 170:1038-1056.

Solaiman et al., "Dirhamnose-lipid production by recombinant nonpathogenic bacterium *Pseudomonas chlororaphis*" (2015) Appl Microbiol Biotechnol 99:4333-4342.

Sotirova et al., "Rhamnolipid—Biosurfactant Permeabilizing Effects on Gram-Positive and Gram-Negative Bacterial Strains", (2008) Curr Microbiol 56:639-644.

Stipcevic et al., "Enhanced healing of full-thickness burn wounds using di-rhamnolipid", (2006) Burns 32:24-34.

Takemoto et al., "Research Note: Inhibition of Fungi from Diseased Grape by Syringomycin E-Rhamnolipid Mixture", (2010) Am. J. Enol. Vitic 61(1): 120-124.

Vatsa et al., "Rhamnolipid Biosurfactants as New Players in Animal and Plant Defense against Microbes", (2010) Int. J. Molecular Sciences 11:5095-5108.

Wang et al., "Engineering Bacteria for Production of Rhamnolipid as an Agent for Enhanced Oil Recovery", (2007) Biotechnology and Bioengineering 98(4):842-853.

Wittgens et al., "Growth independent rhamnolipid production from glucose using the non-pathogenic Pseudomonas putida KT2440", (2011) Microbial Cell Factories 10:80, 17 pages.

Yoo et al., "Characteristics of Microbial Biosurfactant as an Antifungal Agent Against Plant Pathogenic Fungus", (2005) Journal of Microbiology and Biotechnology 15(6):1164-1169.

Zhu et al., "RhlA Converts β-Hydroxyacyl-Acyl Carrier Protein Intermediates in Fatty Acid Synthesis to the β-Hydroxydecanoyl-β-Hydroxydecanoate Component of Rhamnolipids in Pseudomonas aeruginosa", (2008) Journal of Bacteriology 190(9): 3147-3154.

PRODUCTION OF DIRHAMNOSE-LIPID IN RECOMBINANT NONPATHOGENIC BACTERIUM *PSEUDOMONAS CHLORORAPHIS*

This is a National Phase Application filed under 35 U.S.C. 371 as a national stage of PCT/US2014/040652, filed Jun. 3, 2014, and claiming the benefit from of U.S. Provisional Patent Application No. 61/831,776, filed Jun. 6, 2013, the content of each of which is hereby incorporated by reference in its entirety.

BACKGROUND OF THE INVENTION

Field of the Invention

This invention relates to the genes encoding enzymes and regulatory proteins involved in dirhamnose-lipid biosynthesis. This invention also relates to a recombinant, nonpathogenic *Pseudomonas chlororaphis* which is capable of producing $R_1L$ and $R_2L$.

The Sequence Listing submitted in text format (.txt) filed on Nov. 20, 2015, named "SequenceListing.txt", (created on Nov. 19, 2014, 20.2 KB), is incorporated herein by reference.

Description of Related Art

Rhamnolipids are a family of rhamnose-containing glycolipids produced mainly by bacteria in the Pseudomonadaceae family, especially those belonging to the *Pseudomonas* genus. The lipid portion of most rhamnolipids contain 3-hydroxyalkanoyl-3-hydroxyalkanoate ($C_x$-$C_y$, where x and y are the carbon chain lengths of the alkanoate) moiety, though some rhamnolipids may contain only a monomeric 3-hydroxyalkanoate. Furthermore, rhamnolipid could also be synthesized with either one ($R_1L$) or two ($R_2L$) rhamnose molecules. Abdel-Mawgoud at al., 2010, *Applied Microbiology and Biotechnology*, 86:1323-1336, contains a summary of rhamnolipid varieties synthesized by various organisms. The structure of an $R_2L$, i.e., α-L-rhamnopyranosyl-(1→2)-α-L-rhamnopyranosyl-3-hydroxydecanoyl-3-hydroxydecanoate ($R_2$-$C_{10}$-$C_{10}$), as an illustration, follows:

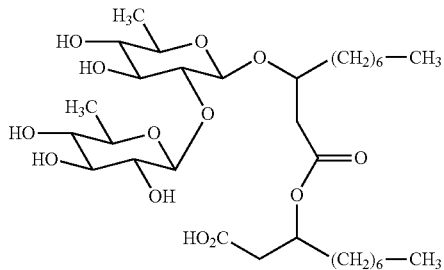

Rhamnolipids have many potential uses, most of which are associated with rhamnolipid's excellent surface-active properties. See, e.g., Faivre and Rosilio 2010, *Expert Opinion on Drug Delivery*, 7:1031-1048; Lourith and Kanlayavattanakul 2009; Nguyen and Sabatini 2011, *International Journal at Cosmetic Science*, 31:255-261; and Pinzon et al. 2009 In Hayes et al. (ed.). *Biobased Surfactants and Detergents: Synthesis, Properties, and Applications*, Chapter 4, pp. 77-105. AOCS Press, Urbana, Ill. Rhamnolipids may also possess valuable biological activities useful in wound healing (see Stipcevic, et al. 2006. *Burns* 32:24-34; see also U.S. Pat. No. 7,262,171), antibacterial (Sotirova, et al. 2008. *Curr. Microbial.* 56:639-644; Vatsa, et al. 2010. *Int. J. Mol. Sci.* 11:5095-5108), and fungicidal (Takemoto, et al. 2010. *Am. J. Enol. Vitic.* 61:120-124; Yoo, et al. 2005. *J. Microbial. Biotechnol.* 15:1164-1169) applications.

A putative metabolic pathway of rhamnolipid biosynthesis in *P. aeruginosa* is shown in FIG. 1. The precursor pool for rhamnolipid synthesis is proposed to be the fatty acid de novo biosynthesis pathway that could provide 3-ketoacyl-acyl carrier-protein (-ACP) metabolites with varying chain length of the acyl group. A β-ketoacyl reductase enzyme (RhlG) coded by the rhlG gene reduces the keto functional group into a hydroxyl group (Campos-García, et al. 1998. *J. of Bacteriology*, 180:4442-4451; Miller, et al. 2006. *J. of Biological Chemistry* 281:18025-18032). Two molecules of 3-hydroxyacyl-ACP are then condensed to yield 3-hydroxyalkanoyl-3-hydroxyalkanoate (3-HHA) by the rhamnosyltransferase A enzyme (RhlA) (Déziel, et al. 2003. *Microbiology* 149:2005-2013; Zhu and Rock 2008. *J. of Bacteriology* 190:3147-3154]. A rhamnose moiety from an activated sugar precursor, dTDP-rhamnose, is attached to 3-HHA to form $R_1L$ via the enzymatic action of rhamnosyltransferase B (RhlB) (Cabrera-Valladares, et al. 2006. *Appl. Microbial. Biotechnol.* 73:187-194). Finally, biosynthesis of $R_2L$ is accomplished by the transfer of another rhamnose moiety from dTDP-rhamnose to $R_1L$ by the action of rhamnosyltransferase C (RhlC) (Cabrera-Valladares, et al. 2006). Biochemical details of certain reaction steps in the pathway are still unclear. For example, it is not clear whether the active form of 3-HHA is attached to an ACP or not. Furthermore, the chemical-energy requirement in terms of high bond-energy molecules (e.g., ATP or dTTP) is not understood, leaving unanswered the question of how the dTDP-rhamnose molecule used as a substrate by RhlB and RhlC is regenerated.

Nevertheless, the overall picture of the metabolic pathway has allowed the genetic manipulation of bacteria to affect rhamnolipid synthesis. An early study demonstrated that several rhamnolipid-nonproducing bacteria (i.e. *P. aeruginosa* PG201, *P. fluorescens* ATC 15453, *P. oleovorans* GPol, *P. putida* KT2442, *Escherichia coli* DH5α, and *E. coli* W2190) could be genetically engineered to produce rhamnolipids through the expression of heterologous rhlA and rhlB genes from *P. aeruginosa* (Ochsner, et al. 1995. *Appl. Environ. Microbiol.* 61:3503-3506: Cabrera-Valladares, et al. 2006). Wang, et al. integrated *P. aeruginosa* rhlA and rhlB genes into the chromosome of *E. coli* BL21(DE3) and *P. aeruginosa* PAO1-rhlA⁻ (Wang, et al. 2007. *Biotechnology and Bioengineering* 98:842-853). While the rhlA-rhlB-complemented *P. aeruginosa* transformant synthesized the same rhamnolipid mixture as that found in the wild-type *P. aeruginosa*, the *E. coli* transformant produced predominantly rhamnolipids having $C_{10}$-$C_{10}$ (ca. 60%) as the lipid component yields. Cha, et al. expressed rhlABRI gene cluster from *P. aeruginosa* EMS1 in *P. putida* 1067 to show production of rhamnolipids without detailing the compositions of the products (Cha, et al. 2008. *Bioresource Technology* 99:2192-2199).

*P. aeruginosa* is the most commonly studied organism for rhamnolipid biosynthesis. Various high-yield strains of *P. aeruginosa* have been adopted for large-scale production (Müller, et al. 2011. *Applied Microbiology and Biotechnology* 89:585-592). In view of rhamnolipid's potential applications in food (see U.S. Pat. No. 5,658,793) and medical (Stipcevic, et al. 2006; see U.S. Pat. No. 7,262,171) areas, a method for producing $R_1L$ using *Pseudomonas chlororaphis*, a nonpathogenic bacterium was previously developed (Gunther, et al. 2005. *Appl. Environ. Microbiol.* 71: 2288-2293; U.S. Pat. No. 7,202,063]. Despite this progress, there is still a need to develop a method for R$_2$L in nonpathogenic bacterium. This invention identifies several genes involved in rhamnolipid biosynthesis and covers recombinant nonpathogenic bacteria capable of producing R$_1$L in a 10-fold improved yield (in comparison to the original *P. chlororaphis* strain described in U.S. Pat. No. 7,202,063) or producing R$_2$L, as a result of introduction of the appropriate DNA into the bacterium, thereby significantly lowering the production cost of R$_1$L and broadening the application sphere of rhamnolipids.

BRIEF SUMMARY OF THE INVENTION

It is an object of this invention to have a polynucleotide encoding rhamnosyltransferase A. It is a further object of this invention that the polynucleotide has the sequence set forth in SEQ ID NO: 12, the full length complement of SEQ ID NO: 12, and the reverse complement of SEQ ID NO: 12. It is also an object of this invention that the polynucleotide has a sequence that is at least 95% identical to the sequence in SEQ ID NO: 12, at least 90% identical to the sequence in SEQ ID NO: 12 and at least 85% identical to the sequence in SEQ ID NO: 12.

It is an object of this invention to have a polynucleotide encoding rhamnosyltransferase A. It is a further object of this invention that the polynucleotide sequence encodes the amino acid sequence set forth in SEQ ID NO: 11, a sequence that is at least 95% identical to the amino acid sequence set forth in SEQ ID NO: 11, a sequence that is at least 90% identical to the amino acid sequence set forth in SEQ ID NO: 11; and a sequence that is at least 85% identical to the amino acid sequence set forth in SEQ ID NO: 11.

It is another object of this invention to have an expression vector containing a polynucleotide that encodes for rhamnosyltransferase A, the nucleotide sequence of SEQ ID NO: 12, the full-length complement of SEQ ID NO: 12, the reverse complement of SEQ ID NO: 12, a sequence that is at least 95% identical to SEQ ID NO: 12, a sequence that is at least 90% identical to SEQ ID NO: 12, a sequence that is at least 85% identical to SEQ ID NO:12, that encodes the amino acid sequence set forth in SEQ ID NO: 11, a sequence that is at least 95% identical to the amino acid sequence set forth in SEQ ID NO: 11, a sequence that is at least 90% identical to the amino acid sequence set forth in SEQ ID NO: 11; and a sequence that is at least 85% identical to the amino acid sequence set forth in SEQ ID NO: 11.

It is another object of this invention to have a recombinant cell that contains an expression vector which contains a polynucleotide that encodes for rhamnosyltransferase A, the nucleotide sequence of SEQ ID NO: 12, the full-length complement of SEQ ID NO: 12, the reverse complement of SEQ ID NO: 12, a sequence that is at least 95% identical to SEQ ID NO: 12, a sequence that is at least 90% identical to SEQ ID NO: 12, a sequence that is at least 85% identical to SEQ ID NO:12, that encodes the amino acid sequence set forth in SEQ ID NO: 11, a sequence that is at least 95% identical to the amino acid sequence set forth in SEQ ID NO: 11, a sequence that is at least 90% identical to the amino acid sequence set forth in SEQ ID NO: 11; and a sequence that is at least 85% identical to the amino acid sequence set forth in SEQ ID NO: 11.

It is a further object of this invention to have a polypeptide that is encoded by a polynucleotide having the sequence of SEQ ID NO: 12, the full-length complement of SEQ ID NO: 12, the reverse complement of SEQ ID NO: 12, a sequence that is at least 95% identical to SEQ ID NO: 12, a sequence that is at least 90% identical to SEQ ID NO: 12, and a sequence that is at least 85% identical to SEQ ID NO: 12.

It is an object of this invention to have an rhamnosyltransferase A polypeptide having the amino acid sequence set forth in SEQ ID NO: 11, an amino acid sequence that is at least 95% identical to SEQ ID NO: 11, an amino acid sequence that is at least 90% identical to SEQ ID NO: 11, and an amino acid sequence that is at least 85% identical to SEQ ID NO: 11.

It is another object of this invention to have an expression vector containing a polynucleotide that encodes for the amino acid sequence set forth in SEQ ID NO: 11, an amino acid sequence that is at least 95% identical to SEQ ID NO: 11, an amino acid sequence that is at least 90% identical to SEQ ID NO: 11, and an amino acid sequence that is at least 85% identical to SEQ ID NO: 11.

It is a further object of this invention to have a recombinant cell containing an expression vector containing a polynucleotide that encodes for the amino acid sequence set forth in SEQ ID NO: 11, an amino acid sequence that is at least 95% identical to SEQ ID NO: 11, an amino acid sequence that is at least 90% identical to SEQ ID NO: 11, and an amino acid sequence that is at least 85% identical to SEQ ID NO: 11.

It is an object of this invention to have a polynucleotide encoding rhamnosyltransferase B. It is a further object of this invention that the polynucleotide has the sequence set forth in SEQ ID NO: 14, the full length complement of SEQ ID NO: 14, and the reverse complement of SEQ ID NO: 14. It is also an object of this invention that the polynucleotide has a sequence that is at least 95% identical to the sequence in SEQ ID NO: 14, at least 90% identical to the sequence in SEQ ID NO: 14, and at least 85% identical to the sequence in SEQ ID NO: 14.

It is an object of this invention to have a polynucleotide encoding rhamnosyltransferase B. It is a further object of this invention that the polynucleotide sequence encodes the amino acid sequence set forth in SEQ ID NO: 13, a sequence that is at least 95% identical to the amino acid sequence set forth in SEQ ID NO: 13, a sequence that is at least 90% identical to the amino acid sequence set forth in SEQ ID NO: 13, and a sequence that is at least 85% identical to the amino acid sequence set forth in SEQ ID NO: 13.

It is another object of this invention to have an expression vector containing a polynucleotide that encodes for rhamnosyltransferase B, the nucleotide sequence of SEQ ID NO: 14, the full-length complement of SEQ ID NO: 14, the reverse complement of SEQ ID NO: 14, a sequence that is at least 95% identical to SEQ ID NO: 14, a sequence that is at least 90% identical to SEQ ID NO: 14, a sequence that is at least 85% identical to SEQ ID NO:14, that encodes the amino acid sequence set forth in SEQ ID NO: 13, a sequence that is at least 95% identical to the amino acid sequence set forth in SEQ ID NO: 13, a sequence that is at least 90% identical to the amino acid sequence set forth in SEQ ID NO: 13, and a sequence that is at least 85% identical to the amino acid sequence set forth in SEQ ID NO: 13.

It is another object of this invention to have a recombinant cell that contains an expression vector which contains a polynucleotide that encodes for rhamnosyltransferase B, the nucleotide sequence of SEQ ID NO: 14, the full-length complement of SEQ ID NO: 14, the reverse complement of SEQ ID NO: 14, a sequence that is at least 95% identical to SEQ ID NO: 14, a sequence that is at least 90% identical to SEQ ID NO: 14, a sequence that is at least 85% identical to SEQ ID NO:14, that encodes the amino acid sequence set forth in SEQ ID NO: 13, a sequence that is at least 95% identical to the amino acid sequence set forth in SEQ ID NO: 13, a sequence that is at least 90% identical to the amino acid sequence set forth in SEQ ID NO: 13, and a sequence that is at least 85% identical to the amino acid sequence set forth in SEQ ID NO: 13.

It is a further object of this invention to have a polypeptide that is encoded by a polynucleotide having the sequence of SEQ ID NO: 14, the full-length complement of SEQ ID NO: 14, the reverse complement of SEQ ID NO 14, a sequence that is at least 95% identical to SEQ ID NO: 14, a sequence that is at least 90% identical to SEQ ID NO: 14, and a sequence that is at least 85% identical to SEQ ID NO: 14.

It is an object of this invention to have a rhamnosyltransferase B polypeptide having the amino acid sequence set forth in SEQ ID NO: 13, an amino acid sequence that is at least 95% identical to SEQ ID NO: 13, an amino acid sequence that is at least 90% identical to SEQ ID NO: 13, and an amino acid sequence that is at least 85% identical to SEQ ID NO: 13.

It is another object of this invention to have an expression vector containing a polynucleotide that encodes for the amino acid sequence set forth in SEQ ID NO: 13, an amino acid sequence that is at least 95% identical to SEQ ID NO: 13, an amino acid sequence that is at least 90% identical to SEQ ID NO: 13, and an amino acid sequence that is at least 85% identical to SEQ ID NO: 13.

It is a further object of this invention to have a recombinant cell containing an expression vector containing a polynucleotide that encodes for the amino acid sequence set forth in SEQ ID NO: 13, an amino acid sequence that is at least 95% identical to SEQ ID NO: 13, an amino acid sequence that is at least 90% identical to SEQ ID NO: 13, and an amino acid sequence that is at least 85% identical to SEQ ID NO: 13.

It is an object of this invention to have a polynucleotide encoding an N-acyl-homoserine lactone-dependent transcription regulator. It is a further object of this invention that the polynucleotide has the sequence set forth in SEQ ID NO: 16, the full length complement of SEQ ID NO: 16, and the reverse complement of SEQ ID NO: 16. It is also an object of this invention that the polynucleotide has a sequence that is at least 95% identical to the sequence in SEQ ID NO: 16, at least 90% identical to the sequence in SEQ ID NO: 16, and at least 85% identical to the sequence in SEQ ID NO: 16.

It is an object of this invention to have a polynucleotide encoding N-acyl-homoserine lactone-dependent transcription regulator. It is a farther object of this invention that the polynucleotide sequence encodes the amino acid sequence set forth in SEQ ID NO: 15, a sequence that is at least 95% identical to the amino acid sequence set forth in SEQ ID NO: 15, a sequence that is at least 90% identical to the amino acid sequence set forth in SEQ ID NO: 15, and a sequence that is at least 85% identical to the amino acid sequence set forth in SEQ ID NO: 15.

It is another object of this invention to have an expression vector containing a polynucleotide that encodes for N-acyl-homoserine lactone-dependent transcription regulator, the nucleotide sequence of SEQ ID NO: 16, the full-length complement of SEQ ID NO: 16, the reverse complement of SEQ ID NO: 16, a sequence that is at least 95% identical to SEQ ID NO: 16, a sequence that is at least 90% identical to SEQ ID NO: 16, a sequence that is at least 85% identical to SEQ ID NO:16, that encodes the amino acid sequence set forth in SEQ ID NO: 15, a sequence that is at least 95% identical to the amino acid sequence set forth in SEQ ID NO: 15, a sequence that is at least 90% identical to the amino acid sequence set forth in SEQ ID NO: 15, and a sequence that is at least 85% identical to the amino acid sequence set forth in SEQ ID NO: 15.

It is another object of this invention to have a recombinant cell that contains an expression vector which contains a polynucleotide that encodes for N-acyl-homoserine lactone-dependent transcription regulator, the nucleotide sequence of SEQ ID NO: 16, the full-length complement of SEQ ID NO: 16, the reverse complement of SEQ ID NO: 16, a sequence that is at least 95% identical to SEQ ID NO: 16, a sequence that is at least 90% identical to SEQ ID NO: 16, a sequence that is at least 85% identical to SEQ ID NO: 16, that encodes the amino acid sequence set forth in SEQ ID NO: 15, a sequence that is at least 95% identical to the amino acid sequence set forth in SEQ ID NO: 15, a sequence that is at least 90% identical to the amino acid sequence set forth in SEQ ID NO: 15, and a sequence that is at least 85% identical to the amino acid sequence set forth in SEQ ID NO: 15.

It is a further object of this invention to have a polypeptide that is encoded by a polynucleotide having the sequence of SEQ ID NO: 16, the full-length complement of SEQ ID NO: 16, the reverse complement of SEQ ID NO: 16, a sequence that is at least 95% identical to SEQ ID NO: 16, a sequence that is at least 90% identical to SEQ ID NO: 16, and a sequence that is at least 85% identical to SEQ ID NO: 16.

It is an object of this invention to have a N-acyl-homoserine lactone-dependent transcription regulator polypeptide having the amino acid sequence set forth in SEQ ID NO: 15, an amino acid sequence that is at least 95% identical to SEQ ID NO: 15, an amino acid sequence that is at least 90% identical to SEQ ID NO: 15, and an amino acid sequence that is at least 85% identical to SEQ ID NO: 15.

It is another object of this invention to have an expression vector containing a polynucleotide that encodes for the amino acid sequence set forth in SEQ ID NO: 15, an amino acid sequence that is at least 95% identical to SEQ ID NO: 15, an amino acid sequence that is at least 90% identical to SEQ ID NO: 15, and an amino acid sequence that is at least 85% identical to SEQ ID NO: 15.

It is a further object of this invention to have a recombinant cell containing an expression vector containing a polynucleotide that encodes for the amino acid sequence set forth in SEQ ID NO: 15, an amino acid sequence that is at least 95% identical to SEQ ID NO: 15, an amino acid sequence that is at least 90% identical to SEQ ID NO: 15, and an amino acid sequence that is at least 85% identical to SEQ ID NO: 15.

It is an object of this invention to have a recombinant cell containing an expression vector which contains a polynucleotide sequence encoding rhamnosyltransferase C. It is a further object of this invention to have a recombinant *Pseudomonas chlororaphis* containing an expression vector which contains a polynucleotide sequence encoding rhamnosyltransferase C, such that the wild-type *P. chlororaphis* lacks the gene encoding rhamnosyltransferase C and such that the recombinant *P. chlororaphis* is capable of producing dirhamnose-lipid.

It is a further object of this invention to have a recombinant *P. chlororaphis* containing an expression vector that encodes a rhamnosyltransferase C operably linked to a promoter such that the recombinant *P. chlororaphis* is capable of producing dirhamnose-lipid.

It is an object of this invention to have a novel method of producing dirhamnose-lipid by transfecting *Pseudomonas chlororaphis* with an expression vector which contains a polynucleotide that encodes rhamnosyltransferase C to produce a recombinant *P. chlororaphis*, and growing the recombinant *P. chlororaphis* in appropriate media for the production of monorhamnose-lipid and dirhamnose-lipid.

It is another object of this invention to have a novel method of producing dirhamnose-lipid by growing a recombinant *P. chlororaphis* in appropriate media. It is a further object of this invention that the recombinant *P. chlororaphis* contains an expression vector which contains a polynucleotide that encodes rhamnosyltransferase C operably linked to a promoter and such that the media is appropriate for the production of monorhamnose-lipid and dirhamnose-lipid.

It is an object of this invention to have a recombinant *Pseudomonas chlororaphis* which contains an expression vector which contains one or more polynucleotides that encode a promoter, a polynucleotide that encodes rhamnosyltransferase A, and a polynucleotide that encodes rhamnosyltransferase B. It is a further object of this invention that the polynucleotide encoding rhamnosyltransferase A and the polynucleotide encoding rhamnosyltransferase B are operably linked to one of the promoters in the expression vector.

It is another object of this invention to have a recombinant *Pseudomonas chlororaphis* which contains an expression vector which contains one or more polynucleotides that encode a promoter, a polynucleotide that encodes rhamnosyltransferase A, and a polynucleotide that encodes rhamnosyltransferase B. It is a further object of this invention that the polynucleotide encoding rhamnosyltransferase A and the polynucleotide encoding rhamnosyltransferase B are operably linked to one of the promoters in the expression vector and that the promoters are P2 promoters.

It is further object of this invention to have a recombinant *Pseudomonas chlororaphis* which contains an expression vector which contains one or more polynucleotides that encode a promoter (one of which is a P2 promoter), a polynucleotide that encodes rhamnosyltransferase A, and a polynucleotide that encodes rhamnosyltransferase B. It is a further object of this invention that the polynucleotide encoding rhamnosyltransferase A and the polynucleotide encoding rhamnosyltransferase B are contiguous and are operably linked to the same P2 promoter.

It is an object of this invention to have a recombinant *Pseudomonas chlororaphis* which contains an expression vector which contains one or more polynucleotides that encode a promoter, a polynucleotide that encodes rhamnosyltransferase A, and a polynucleotide that encodes rhamnosyltransferase B. It is a further object of this invention that the polynucleotide encoding rhamnosyltransferase A is operably linked to a first promoter in the expression vector, and the polynucleotide encoding rhamnosyltransferase B is operably linked to a second promoter in the expression vector, such that the first promoter and the second promoter can be the same promoter or different promoters.

It is a further object of this invention to have a novel method for producing monorhamnose-lipid by *P. chlororaphis* by transfecting *P. chlororaphis* with an expression vector which contains at least one polynucleotide encoding a promoter, a polynucleotide encoding rhamnosyltransferase A, and a polynucleotide encoding rhamnosyltransferase B, such that the polynucleotide encoding rhamnosyltransferase A and the polynucleotide encoding, rhamnosyltransferase B are operably linked to at least one promoter contained within the expression vector (which generates a recombinant *P. chlororaphis*) and growing the recombinant *P. chlororaphis* in an appropriate media (one appropriate for production of monorhamnose lipid by the recombinant *P. chlororaphis*).

It is a further object of this invention to have a novel method for producing monorhamnose-lipid by *P. chlororaphis* by transfecting *P. chlororaphis* with an expression vector which contains at least one polynucleotide encoding a promoter, a polynucleotide encoding rhamnosyltransferase A, and a polynucleotide encoding rhamnosyltransferase B, such that the polynucleotide encoding rhamnosyltransferase A and the polynucleotide encoding rhamnosyltransferase B are operably linked to at least one promoter contained within the expression vector (which generates a recombinant *P. chlororaphis*) and growing the recombinant *P. chlororaphis* in an appropriate media (one appropriate for production of monorhamnose lipid by the recombinant *P. chlororaphis*) under stirring conditions or non-stirring conditions.

It is an object of this invention to have a recombinant cell that contains an expression vector that contains a first promoter operably linked to a first polynucleotide sequence encoding rhamnosyltransferase A, and a second promoter operably linked to a second polynucleotide sequence encoding rhamnosyltransferase C, but the recombinant cell lacks a functioning wild-type rhlA.

It is an object of this invention to have a recombinant cell that contains an expression vector that contains a first promoter operably linked to a first polynucleotide sequence encoding rhamnosyltransferase A, and a second promoter operably linked to a second polynucleotide sequence encoding rhamnosyltransferase C, but the recombinant cell lacks a functioning wild-type rhlA. It is a further object of this invention that the first promoter is an inducible promoter and the second promoter is a constitutive promoter.

It is an object of this invention to have a recombinant cell that contains an expression vector that contains a first promoter operably linked to a first polynucleotide sequence encoding rhamnosyltransferase A, and a second promoter operably linked to a second polynucleotide sequence encoding rhamnosyltransferase C, but the recombinant cell lacks a functioning wild-type rhlA. It is a further object of this invention that the first promoter and the second promoter are different inducible promoters and that different compounds control the expression of the first inducible promoter and the second inducible promoter.

It is an object of this invention to have a recombinant cell that contains a first expression vector that contains a first promoter operably linked to a first polynucleotide sequence encoding rhamnosyltransferase A and a second expression vector that contains a second promoter operably linked to a second polynucleotide sequence encoding rhamnosyltransferase C, but the recombinant cell lacks a functioning wild-type rhlA.

It is an object of this invention to have a recombinant cell that contains a first expression vector that contains a first promoter operably linked to a first polynucleotide sequence encoding rhamnosyltransferase A and a second expression vector that contains a second promoter operably linked to a second polynucleotide sequence encoding rhamnosyltransferase C, but the recombinant cell lacks a functioning wild-type rhlA. It is a further object of this invention that the first promoter is an inducible promoter and the second promoter is a constitutive promoter.

It is another object of this invention to have a recombinant cell that contains a first expression vector that contains a first promoter operably linked to a first polynucleotide sequence encoding rhamnosyltransferase A and a second expression vector that contains a second promoter operably linked to a second polynucleotide sequence encoding rhamnosyltransferase C, but the recombinant cell lacks a functioning wild-type rhlA. It is a further object of this invention that the first promoter and the second promoter are different inducible promoters and that different compounds control the expression of the first inducible promoter and the second inducible promoter.

It is an object of this invention to have a recombinant cell that contains an expression vector that contains a first promoter operably linked to a first polynucleotide sequence encoding rhamnosyltransferase B, and a second promoter operably linked to a second polynucleotide sequence encoding rhamnosyltransferase C, but the recombinant cell lacks a functioning wild-type rhlB.

It is an object of this invention to have a recombinant cell that contains an expression vector that contains a first promoter operably linked to a first polynucleotide sequence encoding rhamnosyltransferase B, and a second promoter operably linked to a second polynucleotide sequence encoding rhamnosyltransferase C, but the recombinant cell lacks a functioning wild-type rhlB. It is a further object of this invention that the first promoter is an inducible promoter and the second promoter is a constitutive promoter.

It is an object of this invention to have a recombinant cell that contains an expression vector that contains a first promoter operably linked to a first polynucleotide sequence encoding rhamnosyltransferase B, and a second promoter operably linked to a second polynucleotide sequence encoding rhamnosyltransferase C, but the recombinant cell lacks a functioning wild type rhlB. It is a further object of this invention that the first promoter and the second promoter are different inducible promoters and that different compounds control the expression of the first inducible promoter and the second inducible promoter.

It is an object of this invention to have a recombinant cell that contains a first expression vector that contains a first promoter operably linked to a first polynucleotide sequence encoding rhamnosyltransferase B and a second expression vector that contains a second promoter operably linked to a second polynucleotide sequence encoding rhamnosyltransferase C, but the recombinant cell lacks a functioning wild-type rhlB.

It is an object of this invention to have a recombinant cell that contains a first expression vector that contains a first promoter operably linked to a first polynucleotide sequence encoding rhamnosyltransferase B and a second expression vector that contains a second promoter operably linked to a second polynucleotide sequence encoding rhamnosyltransferase C, but the recombinant cell lacks a functioning wild-type rhlB. It is a further object of this invention that the first promoter is an inducible promoter and the second promoter is a constitutive promoter.

It is another object of this invention to have a recombinant cell that contains a first expression vector that contains a first promoter operably linked to a first polynucleotide sequence encoding rhamnosyltransferase B and a second expression vector that contains a second promoter operably linked to a second polynucleotide sequence encoding rhamnosyltransferase C, but the recombinant cell lacks a functioning wild-type rhlB. It is a further object of this invention that the first promoter and the second promoter are different inducible promoters and that different compounds control the expression of the first inducible promoter and the second inducible promoter.

It is an object of this invention to have a recombinant cell that contains a first expression vector that contains a first promoter operably linked to both a first polynucleotide sequence encoding rhamnosyltransferase B and a third polynucleotide sequence encoding rhamnosyltransfer A, and a second expression vector that contains a second promoter operably linked to a second polynucleotide sequence encoding rhamnosyltransferase C, but the recombinant cell lacks a functioning wild-type rhlA and rhlB.

It is an object of this invention to have a recombinant cell that contains a first expression vector that contains a first promoter operably linked to both a first polynucleotide sequence encoding rhamnosyltransferase B and a third polynucleotide sequence encoding rhamnosyltransfer A, and a second expression vector that contains a second promoter operably linked to a second polynucleotide sequence encoding rhamnosyltransferase C, but the recombinant cell lacks a functioning wild-type rhlA and rhlB. It is a further object of this invention that the first promoter is an inducible promoter and the second promoter is a constitutive promoter.

It is an object of this invention to have a recombinant cell that contains a first expression vector that contains a first promoter operably linked to both a first polynucleotide sequence encoding rhamnosyltransferase B and a third polynucleotide sequence encoding rhamnosyltransfer A, and a second expression vector that contains a second promoter operably linked to a second polynucleotide sequence encoding rhamnosyltransferase C, but the recombinant cell lacks a functioning wild-type rhlA and rhlB. It is a further object of this invention that the first promoter and the second promoter are different inducible promoters and that different compounds control the expression of the first inducible promoter and the second inducible promoter.

It is an object of this invention to have a recombinant cell that contains an expression vector that contains a first promoter operably linked to a first polynucleotide sequence encoding rhamnosyltransferase A and rhamnosyltransferase B, and a second promoter operably linked to a second polynucleotide sequence encoding rhamnosyltransferase C, but the recombinant cell lacks a functioning wild-type rhlA and rhlB.

It is an object of this invention to have a recombinant cell that contains an expression vector that contains a first promoter operably linked to a first polynucleotide sequence encoding rhamnosyltransferase A and rhamnosyltransferase B, and a second promoter operably linked to a second polynucleotide sequence encoding rhamnosyltransferase C, but the recombinant cell lacks a functioning wild-type rhlA and rhlB. It is a further object of this invention that the first promoter is an inducible promoter and the second promoter is a constitutive promoter.

It is an object of this invention to have a recombinant cell that contains an expression vector that contains a first promoter operably linked to a first polynucleotide sequence encoding rhamnosyltransferase A and rhamnosyltransferase B, and a second promoter operably linked to a second polynucleotide sequence encoding rhamnosyltransferase C, but the recombinant cell lacks a functioning wild-type rhlA and rhlB. It is a further object of this invention that the first promoter and the second promoter are different inducible promoters and that different compounds control the expression of the first inducible promoter and the second inducible promoter.

It is a further object of this invention to have a method for controlling the ratio of monorhamnose lipid to dirhamnose lipid produced by a recombinant cell. In particular the recombinant cell contains an expression vector that contains an inducible promoter operably linked to a first polynucleotide encoding rhamnosyltransferase A and a constitutive promoter operably linked to a second polynucleotide encoding rhamnosyltransferase C, but lacks a functioning wild-type rhlA. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue. It is another object of this invention that the recombinant cell has a functioning wild-type rhlB.

It is another object of this invention to have a method for controlling the ratio of monorhamnose lipid to dirhamnose lipid produced by a recombinant cell. In particular the recombinant cell contains an expression vector that contains an inducible promoter operably linked to a first polynucleotide encoding rhamnosyltransferase B and a constitutive promoter operably linked to a second polynucleotide encoding rhamnosyltransferase C, but lacks a functioning wild-type rhlB. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue. It is another object of this invention that the recombinant cell has a functioning wild-type rhlA.

It is a further object of this invention to have a method for controlling the ratio of monorhamnose lipid to dirhamnose lipid produced by a recombinant cell. In particular the recombinant cell contains an expression vector that contains an inducible promoter operably linked to a first polynucleotide encoding rhamnosyltransferase A and rhamnosyltransferase B and a constitutive promoter operably linked to a second polynucleotide encoding rhamnosyltransferase C, but lacks a functioning wild-type rhlA and rhlB. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue.

It is a further object of this invention to have a method for controlling the ratio of monorhamnose lipid to dirhamnose lipid produced by a recombinant cell. In particular the recombinant cell contains a first expression vector that contains an inducible promoter operably linked to a first polynucleotide encoding rhamnosyltransferase A and a second expression vector that contains a constitutive promoter operably linked to a second polynucleotide encoding rhamnosyltransferase C, but lacks a functioning wild-type rhlA. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue. It is another object of this invention that the recombinant cell has a functioning wild-type rhlB.

It is another object of this invention to have a method for controlling the ratio of monorhamnose lipid to dirhamnose lipid produced by a recombinant cell. In particular the recombinant cell contains a first expression vector that contains an inducible promoter operably linked to a first polynucleotide encoding rhamnosyltransferase B and a second expression vector that contains a constitutive promoter operably linked to a second polynucleotide encoding rhamnosyltransferase C, but lacks a functioning wild-type rhlB. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue. It is another object of this invention that the recombinant cell has a functioning wild-type rhlA.

It is a further object of this invention to have a method for controlling the ratio of monorhamnose lipid to dirhamnose lipid produced by a recombinant cell. In particular the recombinant cell contains a first expression vector that contains an inducible promoter operably linked to a first polynucleotide encoding rhamnosyltransferase A and rhamnosyltransferase B and a second expression vector containing a constitutive promoter operably linked to a second polynucleotide encoding rhamnosyltransferase C, but lacks a functioning wild-type rhlA and rhlB. The method involves culturing the recombinant cell in a media appropriate for production of rhamnolipids, adding a compound that controls the expression of the inducible promoter, and removing the compound that controls the expression of the inducible promoter at an appropriate time such that the production of monorhamnose-lipid decreases or stops but production of dirhamnose-lipid is able to continue.

It is a further object of this invention to have a method for controlling the ratio of monorhamnose lipid to dirhamnose lipid produced by a recombinant cell. In particular the recombinant cell contains an expression vector that contains a first inducible promoter operably linked to a first polynucleotide encoding rhamnosyltransferase A and a second inducible promoter operably linked to a second polynucleotide encoding rhamnosyltransferase C, but lacks a functioning wild-type rhlA. The method involves culturing the recombinant cell in a media appropriate for production of rhamnolipids, adding a first compound that controls the expression of the first inducible promoter, adding a second compound that controls the expression of the second inducible promoter at a first appropriate time, and removing the first compound that controls the expression of the first inducible promoter at a second appropriate time such that the production of monorhamnose-lipid decreases or stops but production of dirhamnose-lipid is able to continue and such that the first appropriate time and the second appropriate time and either may precede or be subsequent to each other. It is another object of this invention that the recombinant cell has a functioning wild-type rhlB.

It is a further object of this invention to have a method for controlling the ratio of monorhamnose lipid to dirhamnose lipid produced by a recombinant cell. In particular the recombinant cell contains an expression vector that contains a first inducible promoter operably linked to a first polynucleotide encoding rhamnosyltransferase B and a second inducible promoter operably linked to a second polynucleotide encoding rhamnosyltransferase C, but lacks a functioning wild-type rhlB. The method involves culturing the recombinant cell in a media appropriate for production of rhamnolipids, adding a first compound that controls the expression of the first inducible promoter, adding a second compound that controls the expression of the second inducible promoter at a first appropriate time, and removing the first compound that controls the expression of the first inducible promoter at a second appropriate time such that the production of monorhamnose-lipid decreases or stops but production of dirhamnose-lipid is able to continue and such that the first appropriate time and the second appropriate time and either may precede or be subsequent to each other. It is another object of this invention that the recombinant cell has a functioning wild-type rhlA.

It is a further object of this invention to have a method for controlling the ratio of monorhamnose lipid to dirhamnose lipid produced by a recombinant cell. In particular the recombinant cell contains an expression vector that contains a first inducible promoter operably linked to a first polynucleotide encoding rhamnosyltransferase A and rhamnosyltransferase B, and a second inducible promoter operably linked to a second polynucleotide encoding rhamnosyltransferase C, but lacks a functioning wild-type rhlA and rhlB. The method involves culturing the recombinant cell in a media appropriate for production of rhamnolipids, adding a first compound that controls the expression of the first inducible promoter, adding a second compound that controls the expression of the second inducible promoter at a first appropriate time, and removing the first compound that controls the expression of the first inducible promoter at a second appropriate time such that the production of monorhamnose-lipid decreases or stops but production of dirhamnose-lipid is able to continue and such that the first appropriate time and the second appropriate time and either may precede or be subsequent to each other.

It is a further object of this invention to have a method for controlling the ratio of monorhamnose lipid to dirhamnose lipid produced by a recombinant cell. In particular the recombinant cell contains a first expression vector that contains a first inducible promoter operably linked to a first polynucleotide encoding rhamnosyltransferase A and a second expression vector that contains a second inducible promoter operably linked to a second polynucleotide encoding rhamnosyltransferase C, but lacks a functioning wild-type rhlA. The method involves culturing the recombinant cell in a media appropriate for production of rhamnolipids, adding to the media a first compound that controls the expression of the first inducible promoter, adding a second compound that controls the expression of the second inducible promoter to the media at a first appropriate time, and removing the first compound that controls the expression of the first inducible promoter from the media at second appropriate time such that the first appropriate time is independent of and may precede or be subsequent to the second appropriate time. It is another object of this invention that the recombinant cell has a functioning wild-type rhlB.

It is a further object of this invention to have a method for controlling the ratio of monorhamnose lipid to dirhamnose lipid produced by a recombinant cell. In particular the recombinant cell contains a first expression vector that contains a first inducible promoter operably linked to a first polynucleotide encoding rhamnosyltransferase B and a second expression vector that contains a second inducible promoter operably linked to a second polynucleotide encoding rhamnosyltransferase C, but lacks a functioning wild-type rhlB. The method involves culturing the recombinant cell in a media appropriate for production of rhamnolipids, adding to the media a first compound that controls the expression of the first inducible promoter, adding a second compound that controls the expression of the second inducible promoter to the media at a first appropriate time, and removing the first compound that controls the expression of the first inducible promoter from the media at second appropriate time such that the first appropriate time is independent of and may precede or be subsequent to the second appropriate time. It is another object of this invention that the recombinant cell has a functioning wild-type rhlA.

It is a further object of this invention to have a method for controlling the ratio of monorhamnose lipid to dirhamnose lipid produced by a recombinant cell. In particular the recombinant cell contains a first expression vector that contains a first inducible promoter operably linked to a first polynucleotide encoding both rhamnosyltransferase A and rhamnosyltransferase B, and a second expression vector that contains a second inducible promoter operably linked to a second polynucleotide encoding rhamnosyltransferase C, but lacks a functioning wild-type rhlA and rhlB. The method involves culturing the recombinant cell in a media appropriate for production of rhamnolipids, adding to the media a first compound that controls the expression of the first inducible promoter, adding a second compound that controls the expression of the second inducible promoter to the media at a first appropriate time, and removing the first compound that controls the expression of the first inducible promoter from the media at second appropriate time such that the first appropriate time is independent of and may precede or be subsequent to the second appropriate time.

It is an object of this invention to have a recombinant *Pseudomonas chlororaphis* containing an expression vector which contains a promoter operably linked to a polynucleotide that encodes an N-acyl-homoserine lactone dependent transcription regulator from *P. chlororaphis* subsp. *aureofaciens*, such that the recombinant *P. chlororaphis* produces monorhamnose-lipid under stirring conditions. It is a further object of this invention that the recombinant *P. chlororaphis* contains functioning rhlA and rhlB.

It is an object of this invention to have a recombinant *Pseudomonas chlororaphis* containing an expression vector which contains a promoter operably linked to a polynucleotide that encodes an N-acyl-homoserine lactone dependent transcription regulator from *P. chlororaphis* subsp. *aureofaciens* and contains a promoter operably linked to a polynucleotide encoding rhamnosyltransferase C, such that the recombinant *P. chlororaphis* produces monorhamnose-lipid and dirhamnose-lipid under stirring conditions. It is a further object of this invention that the recombinant *P. chlororaphis* contains functioning rhlA and rhlB.

It is an object of this invention to have a recombinant *Pseudomonas chlororaphis* containing a first expression vector which contains a promoter operably linked to a polynucleotide that encodes an N-acyl-homoserine lactone dependent transcription regulator from *P. chlororaphis* subsp. *aureofaciens* and contains a second expression vector which contains a promoter operably linked to a polynucleotide encoding rhamnosyltransferase C, such that the recombinant *P. chlororaphis* produces monorhamnose-lipid and dirhamnose-lipid under stirring conditions. It is a further object of this invention that the recombinant *P. chlororaphis* contains functioning rhlA and rhlB.

A method for producing monorhamnose-lipid under stirring conditions comprising culturing a recombinant *Pseudomonas chlororaphis* in appropriate media under stirring conditions. The recombinant *P. chlororaphis* contains an expression vector which contains a promoter operably linked to a polynucleotide that encodes an N-acyl-homoserine lactone dependent transcription regulator from *P. chlororaphis* subsp. *aureofaciens*, and contains functioning rhlA and rhlB.

A method for producing monorhamnose-lipid and dirhamnose-lipid under stirring conditions comprising culturing a recombinant *Pseudomonas chlororaphis* in appropriate media under stirring conditions. The recombinant *P. chlororaphis* contains an expression vector which contains a promoter operably linked to a polynucleotide that encodes an N-acyl-homoserine lactone dependent transcription regulator from *P. chlororaphis* subsp. *aureofaciens* and a promoter operably linked to polynucleotide encoding rhamnosyltransferase C, and contains functioning rhlA and rhlB.

A method for producing monorhamnose-lipid and dirhamnose-lipid under stirring conditions comprising culturing a recombinant *Pseudomonas chlororaphis* in appropriate media under stirring conditions. The recombinant *P. chlororaphis* contains a first expression vector which contains a promoter operably linked to a polynucleotide that encodes an N-acyl-homoserine lactone dependent transcription regulator from *P. chlororaphis* subsp. *aureofaciens*, a second expression vector which contains a promoter operably linked to polynucleotide encoding rhamnosyltransferase C, and functioning rhlA and rhlB.

BRIEF DESCRIPTION OF THE FIGURES

In FIG. 2, acnB is a (3'-partial) aconitate hydratase gene; rhlA$_{Pch}$ is rhamnosyltransferase A (where Pch=*P. chlororaphis*); rhlB$_{Pch}$ is rhamnosyltransferase B; rhlR$_{Pch}$ is N-acyl-homoserine lactone-dependent transcription regulator; and RBS is ribosomal-binding-site.

DETAILED DESCRIPTION OF THE INVENTION

Figure 1:
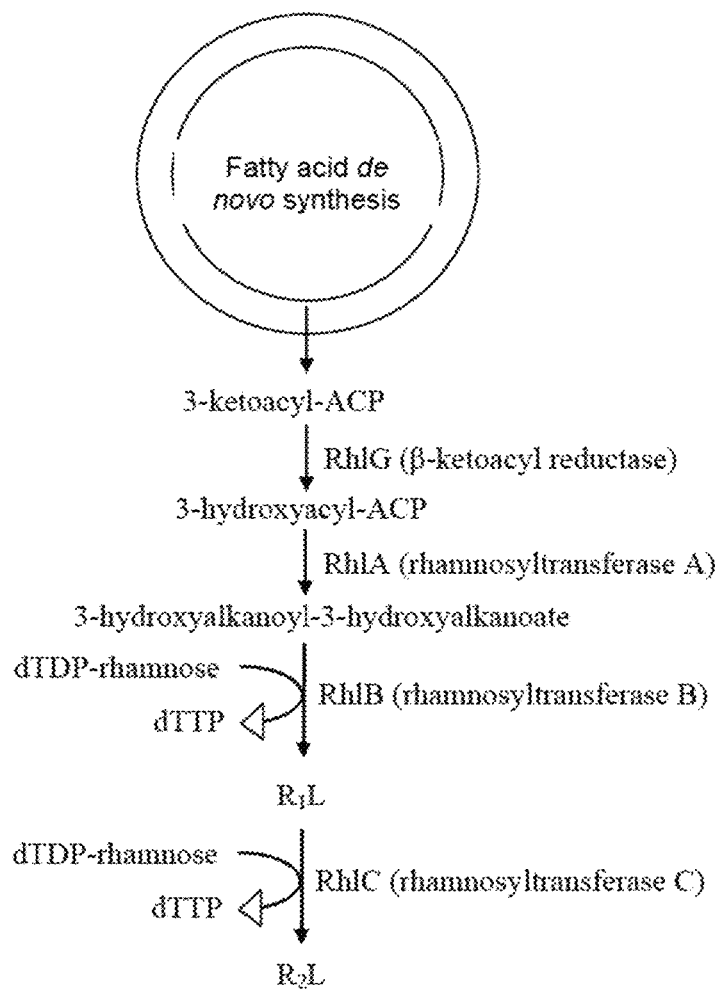
FIG. 1 is the putative metabolic pathway of rhamnolipid biosynthesis.

A "protein" or "polypeptide" is a chain of amino acids arranged in a specific order determined by the coding sequence in a polynucleotide encoding the protein or polypeptide. Each protein or polypeptide has a unique function.

The expression "heterologous nucleic acid sequence", "heterologous polynucleotide" or "heterologous gene" as used herein, refers to a gene or polynucleotide or nucleic acid sequence that is not in its natural environment (in other words, has been altered by the hand of man). In an exemplary embodiment, a heterologous polynucleotide is a polynucleotide from one species that is introduced into another species. In another exemplary embodiment, a heterologous polynucleotide can be a nucleic acid sequence joined to a regulatory element(s) e.g., a promoter, that is not found naturally associated with the polynucleotide. Heterologous genes, heterologous polynucleotides, heterologous nucleic acid sequences are typically produced using recombinant DNA techniques.

The terms "isolated", "purified", or "biologically pure" as used herein, refer to material that is substantially or essentially free from components that normally accompany the material in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

Unless otherwise indicated a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al. 1991. *Nucleic Acid Res.* 19:5081; Ohtsuka et al. 1985. *J. Biol. Chem.* 260:2605-2608; and Rossolini et al. 1994, *Mol. Cell. Probes* 8:91-98).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide.

The term "label" as used herein, refers to a composition detectable by spectroscopic, photochemical, biochemical, immunochemical, or chemical means. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "probe" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically a DNA oligonucleotide of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of a promoter complex sequence will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant or wild-type) form of the cell or express native genes that are otherwise abnormally expressed, over expressed, under expressed or not expressed at all.

The terms "transgenic", "transformed", "transformation", "transformed" and "transfection" are similar in meaning to "recombinant". "Transformation", "transgenic", and "transfection" refers to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subject for a period of time to one or more conditions which require the transcription of some or all of transferred polynucleotide in order for the transgenic organism or cell to live and/or grow. Polynucleotides that are transformed into a cell but are not integrated into the host's chromosome remain as an expression vector within the cell. One may need to grow the cell under certain conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A method of selecting an isolated polynucleotide that affects the level of expression of a polypeptide in a virus or in a host cell (eukaryotic, such as plant, yeast, fungi, or algae; prokaryotic, such as bacteria) may include the steps of: constructing an isolated polynucleotide of the present invention; introducing the isolated polynucleotide into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

An "expression cassette" as used herein, refers to a nucleic acid construct, typically generated recombinantly or synthetically, which comprises a series of specified nucleic acid elements that permit transcription of a particular nucleic acid in a host cell.

Typically, an "expression cassette" is part of an "expression vector". An expression vector or simply a "vector", as used herein, refers to nucleic acid capable of replicating in a selected host cell or organism. An expression vector can replicate as an autonomous structure, or alternatively can integrate into the host cell chromosomes or the nucleic acids of an organelle, and thus replicate along with the host cell genuine. Thus, an expression vector are polynucleotides capable of replicating in a selected host cell, organelle, or organism, e.g., a plasmid, virus, artificial chromosome, nucleic, acid fragment, and for which certain genes on the expression vector are transcribed and translated into a polypeptide or protein within the cell, organelle or organism; or any suitable construct known in the art, which comprises an "expression cassette".

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a nucleic acid of interest. Hybridization of the first and second nucleic acids is conducted under standard stringent conditions, e.g., high temperature and/or low salt content, which tend to disfavor hybridization of dissimilar nucleotide sequences.

Any expression vector containing the polynucleotides described herein operably linked to a promoter is also covered by this invention. A polynucleotide sequence is operably linked to an expression control sequence(s) (e.g., a promoter and, optionally, an enhancer) when the expression control sequence controls and regulates the transcription and translation of that polynucleotide sequence. An expression vector is a replicon, such as plasmid, phage or cosmid, and which contains the desired polynucleotide sequence operably linked to the expression control sequence(s). The promoter may be, or is identical to, a viral, phage, bacterial, yeast, insect, plant, or mammalian promoter. Similarly, the enhancer may be the sequences of an enhancer from virus, phage, bacteria, yeast, insects, plants, or mammals.

The term "operably linked" refers to the association of two or more nucleic acid fragments on a single polynucleotide so that the function of one is affected by the other. For example, a promoter is operably linked with a coding sequence so that the promoter is capable of affecting the expression of that coding sequence (i.e., that the coding sequence is under the transcriptional control of the promoter). Coding sequences can be operably linked to regulatory sequences in sense or antisense orientation. When a promoter is operably linked to a polynucleotide sequence encoding a protein or polypeptide, the polynucleotide sequence should have an appropriate start signal (e.g., ATG) in front of the polynucleotide sequence to be expressed. Further, the sequences should be in the correct reading frame to permit transcription of the polynucleotide sequence under the control of the expression control sequence and, translation of the desired polypeptide or protein encoded by the polynucleotide sequence. If a gene or polynucleotide sequence that one desires to insert into an expression vector does not contain an appropriate start signal, such a start signal can be inserted in front of the gene or polynucleotide sequence. In addition, a promoter can be operably linked to a RNA gene encoding a functional RNA.

The following terms are used to describe the sequence relationships between two or more nucleic acids or polynucleotides: "reference sequence", "comparison window", "sequence identity", "percentage of sequence identity", and "substantial identity". A reference sequence is a defined sequence used as a basis for a sequence comparison; a reference sequence may be a subset of a larger sequence, or gene sequence given in a sequence listing.

The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is it least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl., Acad. Sci USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984. *Nuc. Acids Res.* 12:387-395.

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, 1989. *Proc. Natl. Acad. Sci. USA* 89:10915) alignments (B) of 50, expectation (E) of 10, M=5, N=4, and a comparison of both strands.

The BLAST algorithm also performs a statistical analysis of the similarity between two sequences (see, e.g., Karlin and Altschul, 1993. *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively hybridizes to" or "specifically hybridizes to" refers to the binding, duplexing or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This situation can occur, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

This invention utilizes routine techniques in the field of molecular biology. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994). Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981). Using of machines for sequencing DNA or RNA is known in the art field.

A "cell" includes prokaryotic cells, eukaryotic cells, viruses, fungi, and other similar organisms. Bacteria are an example of prokaryotic cells. Plants, algae, mammals, birds, fish, reptiles, amphibians are examples of eukaryotic organisms that have cells.

Turning now to the invention described herein, genes encoding rhamnosyltransferase A and rhamnosyltransferase B (rhlA and rhlB, respectively) present in *Pseudomonas chlororaphis* NRRL B-30761 are isolated and sequenced. In addition, the gene encoding N-acyl-homoserine lactone-dependent transcription regulator (rhlR) is also isolated and sequenced. It is discovered that *P. chlororaphis* NRRL B-30761 lacks the gene encoding rhamnosyltransferase C which could possibly explain why *P. chlororaphis* NRRL B-30761 does not produce dirhamnose-lipid. The gene for rhamnosyltransferase C (rhlC) is isolated from another bacteria, is sequenced, and is placed in an expression vector which is subsequently transfected into *P. chlororaphis* NRRL B-30761. The recombinant *P. chlororaphis* NRRL B-30761 is then able to produce dirhamnose-lipid.

Example 1 Cloning and Characterization of rhlA, rhlB, and rhlR

*Pseudomonas chlororaphis* NRRL B-30761 is a non-pathogenic organism that produces monorhamnolipids ($R_1L$) (U.S. Pat. No. 7,202,063). Genetic characterization of this strain is undertaken to facilitate metabolic engineering effort to improve its rhamnolipid biosynthesis potential both in terms of product yield and structural variety. The genes responsible for $R_1L$ synthesis, rhamnosyltransferase A and B (rhlA and rhlB, respectively) are cloned and characterized using a PCR approach described previously (Solaiman 2000. *Biotechnol. Lett.* 22:789-794; Solaiman, et al. 2008, *J. of Industrial Microbiology and Biotechnology* 35:111-120). Prior to initiating cloning of rhlA and rhlB, sequence alignment analysis is performed on the reported sequences of rhlA and rhlB of *Burkholderia pseudomallei* K96243 (gi 53721039), *Burkholderia mallei* ATCC 23344 (gi 53715870), *Pseudomonas aeruginosa* PAO1 (gi 15595198), *P. aeruginosa* PAO1 (gi 9949611) and *P. aeruginosa* DSM 2659 (gi 452502). From the highly conserved regions identified in the aligned sequences, a set of degenerative PCR primers (A1, A2, A3 and A4; Table 1) is generated to perform nested PCR amplification.

TABLE 1

| Primer | Sequence (5' → 3') |
|---|---|
| A1 | GTSAACGGCGCGMTGGCGAC (SEQ ID NO: 1) |
| A2 | GCRTTGTCGAACTGRTCGTG (SEQ ID NO: 2) |
| A3 | ACSAAGGACGACGAGGTGGA (SEQ ID NO: 3) |
| A4 | KGCTGSGSCGGCGCGAACCA (SEQ ID NO: 4) |

Primers A1 and A2 are used in the first-round PCR using Taq DNA polymerase (New England Biolabs, Ipswich, Mass.) per supplier's instructions with the following thermal-cycling program: 94° C., 5 minutes; 42° C. 1 minute; 72° C., 2 minutes; then 30 cycles of [94° C., 40 seconds; 55° C., 40 seconds; 72° C. 1 minute]; and finally 72° C. 7 minutes. The resultant reaction product mixture is used as templates for the ensuing nested PCR using primers A3 and A4 and performed under the same conditions as described.

Figure 2:
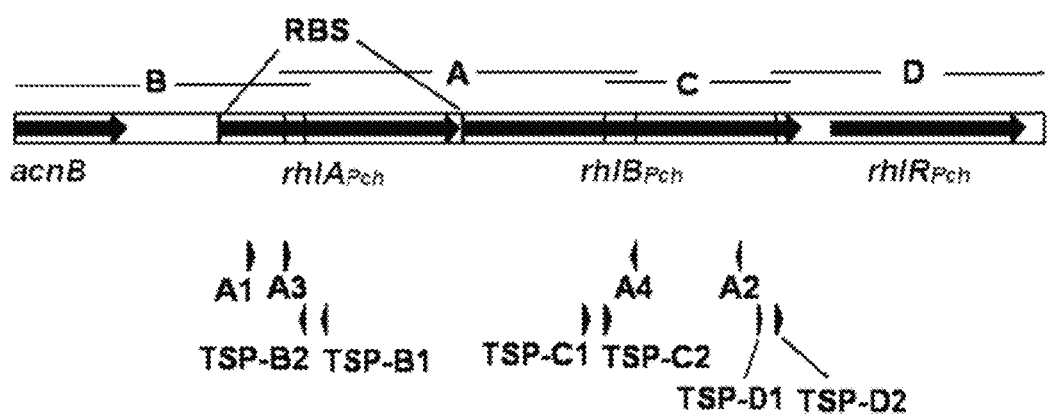
FIG. 2 is the gene locus of *P. chlororaphis* NRRL B-30761 showing the relative positions of amplicons A, B, C, and D.

The PCR amplification generated amplicon A which is 1.33-kb and spans the 3'-end of rhamnosyltransferase A (rhlA$_{Pch}$) and the 5'-end of rhamnosyltransferase B (rhlB$_{Pch}$) genes of *P. chlororaphis*. See FIG. 2. The nucleotide sequence of amplicon A is determined on Applied Biosystems 3730 DNA Analyzer (Life Technologies Corp., Carlsbad, Calif.) using manufacturer's instructions. Two sets of target-specific primers are generated based on the sequence of amplicon A. These target-specific primers are used to amplify the flanking genomic sequences by a chromosomal gene walking approach using Seegene's DNA Walking Speedup Kit (Rockville, Md.) per manufacturer's instructions. One set of the target-specific primers, TSP-B1 (5'-CCAGGCGCAAACGACATCAC-3' (SEQ ID NO: 5)) and TSP-B2 (5'-CCCAGGACACGGAAACCAAG-3' (SEQ ID NO: 6)), are used to obtain amplicon B which is 1.1 kb long (see FIG. 2). Amplicon B is sequenced on Applied Biosystems 3730 DNA Analyzer (Life Technologies Corp., Carlsbad, Calif.) using manufacturer's instructions to obtain its nucleotide sequence. Another set of target-specific primers, TSP-C1 (5'-GGCGCTTGCCATTGACTCTG-3' (SEQ ID NO: 7)) and TSP-C2 (5'-CAACGCACTACGCCACAAAC-3' (SEQ ID NO: 8)), are used to obtain amplicon C which is 0.7 kb long (see FIG. 2). Amplicon C is also sequenced on Applied Biosystems 3730 DNA Analyzer (Life Technologies Corp., Carlsbad, Calif.) using manufacturer's instructions. A third set of target-specific primers, TSP-D1 (5'-CTGGACGATGCGATCACAACG-3' (SEQ ID NO: 9)) and TSP-D2 (5'-CTGCGACGCTGCCTCTTGIGAA-3' (SEQ. ID NO: 10)) are designed based on the sequence of amplicon C and are used to generate amplicon D (1.02 kb) which is also sequenced on Applied Biosystems 3730 DNA Analyzer (Life Technologies Corp., Carlsbad, Calif.) using manufacturer's instructions. The sequences of amplicons A, B, C and D are assembled into a contiguous 3,900 bp-long sequence (GenBank accession number JN415770). Four potential gene sequences are identified through an open-reading-flame search using PC-based Clone Manager 9 (Scientific and Educational Software, Cary, N.C.). Based on similarity analyses of these DNA sequences using BLAST, the contiguous sequence is annotated with a partial C-terminal portion) aconitate hydratase gene (acnB), and the complete $rhlA_{Pch}$ (894 bps, SEQ ID NO: 12), $rhlB_{Pch}$ (1,272 bps, SEQ ID NO: 14), and $rhlR_{Pch}$ (726 bps, SEQ ID NO: 16) (see FIG. 2).

A comparison of the structural features of the gene-products of $rhlA_{Pch}$ (i.e., $RhlA_{Pch}$), $rhlB_{Pch}$ (i.e., $RhlB_{Pch}$), and $rhlR_{Pch}$ (i.e., $RhlR_{Pch}$) is performed with proteins having some sequence homology and that are published in GenBank. BLASTP analysis reveals that the putative amino-acid sequence of $RhlA_{Pch}$ (297 residues, SEQ ID NO: 11) is only 63% identical (in a 278 amino acid highly conserved segment) to its closest-matched $RhlA_{Pae}$ sequence of P. aeruginosa (GenBank Accesion No. AAG06867). The highly conserved 278 amino acid region contains an alpha/beta-hydrolase domain likely to be important for enzyme activity. The C-terminus (17 amino acids) of $RhlA_{Pch}$ lacks appreciable similarity to $RhlA_{Pae}$ C-terminus, and the BLASTP analysis fails to identify a sequence having high similarity. RhlA catalyzes the reaction of two molecules of 3-hydroxyacyl-acyl carrier protein (ACP) to form 3-hydroxyalkanoyl-3-hydroxyalkanoate (Zhu and Rock, 2008. *J. of Bacteriology* 190:3147-3154) that is then incorporated into rhamnolipid. RhlA thus catalyzes the first committed step of rhamnolipid biosynthesis (Déziel, et al. 2003. *Microbiology* 149:2005-2013; Van Gennip, et al. 2009. *Acta Pathologica, Microbiologica., et Innnunologica Scandinavica* 117:537-546).

Not wishing to be bound to any particular theory, the dissimilarity of the amino acid sequence of $RhlA_{Pch}$ to the corresponding enzyme in P. aeruginosa could explain the observation that P. chlororaphis synthesizes rhamnolipid having mostly 3-hydroxydodecanoyl-3-hydroxydecanoate ($C_{12}$-$C_{10}$) (30%) or 3-hydroxydodecenoyl-3-hydroxydodecanoate ($C_{12:1}$-$C_{10}$) (40%) as its lipid component (Gunther, et al. 2005), in contrast to the major rhamnolipids of P. aeruginosa containing primarily 3-hydroxydecanoyl-3-hydroxydecanoate ($C_{10}$-$C_{10}$) (Zhu and Rock, 2008: Abdel-Mawgoud, et al. 2010). This hypothesis provides support to an earlier hypothesis that the type of fatty acids incorporated into rhamnolipid is dictated in part by the specificity of RhlA, and not by the relative abundance of the fatty acid precursors (Cabrera-Valladares, et al. 2006).

RhlB enzyme catalyzes the transfer of the first L-rhamnose moiety from dTDP-L-rhamnose onto the dimeric hydroxyfatty acid entity of rhamnolipid (Cabrera-Valladares, et al. 2006). A BLASTP analysis of $RhlB_{Pch}$ (423 amino acid; SEQ ID NO: 13) indicates that $RhlB_{Pch}$ has 63% identical (74% positives) amino acid residues to those of its closest-matched counterpart, $RhlB_{Pae}$ (426 amino acid) of P. aeruginosa (GenBank Accesion No. YP_001347032.1). The entire length of $RhlB_{Pch}$ has a conserved protein domain that belongs to the GTB-type superfamily of glycosyltransferases (Marchler-Bauer, et al. 2011. *Nucleic Acids Res.* 39:D225-D229). These glycosyltransferases are typically characterized by two structurally conserved (but not necessarily amino acid sequence homologous) domains separately located at the N- and C-termini of the protein, with the cleft region between the two domains containing the catalytic site. Again, not wishing to be bound to any particular hypothesis, the degree of sequence dissimilarity between $RhlB_{Pch}$ and $RhlB_{Pae}$ may partially account for their respective reactivity toward $C_{12}$-$C_{10}$/$C_{12:1}$-$C_{10}$ and $C_{10}$-$C_{10}$ in the $R_1L$ synthesis step of the pathway.

RhlR is an N-acyl-homoserine lactone-dependent transcription regulator protein that controls the transcription of rhlA and rhlB genes via the rhl quorum-sensing circuitry (Chen, et al. 2004. *Biotechnology Progress*, 20:1325-1331; Dekimpe and Déziel 2009. *Microbiology* 155:712-723). Sequence comparison of $RhlR_{Pch}$ (241 amino acid, SEQ ID NO: 15) and its closest homologue $RhlR_{Pch-au}$ of P. chlororaphis subsp. aureofaciens (241 amino acid; GenBank Accession No. AAK73190) by BLASTP demonstrates only 66% identical amino acid over the entire length of the protein. Not wishing to be bound by one particular hypothesis, this structural diversity may well translate into functional difference that leads to the observation that rhamnolipid is only synthesized by P. chlororaphis NRRL B-30761 grown under non-stirring conditions.

Example 2 Absence of rhlC in P. chlororaphis

It is hypothesized that the lack of $R_2L$ in P. chlororaphis NRRL B-30761 is caused by the absence of rhlC coding for the enzyme that catalyzes the addition of rhamnose moiety onto $R_1L$ (Cabrera-Valladares, et al. 2006). Using PCR, the presence of rhlC in strain P. chlororaphis NRRL B-30761 is examined. Degenerate, nested PCR primers ($1^{st}$-round forward primer CL13-131-C8 (SEQ ID NO: 17) and reverse primer CL13-131-D36 (SEQ ID NO: 18), $2^{nd}$-round (i.e., nested) forward primer CL13-131-C5 (SEQ ID NO: 19) and reverse primer CL13-131-D34 (SEQ ID NO: 20)) are designed based on alignment analysis of known rhlC genes in GenBank, and tested on P. aeruginosa PAO1 (provided by Dr. P. Castric, Duquesne University, Pittsburgh, Pa.) and PG201 strains. PCR is performed using Taq DNA polymerase (New England Biolabs, Ipswich, Mass.) with the following thermal-cycling program: 94° C., 5 minutes; 42° C., 1 minute; 72° C., 2 minutes; then 30 cycles of [94° C., 40 seconds; 55° C., 40 seconds; 72° C., 1 minute]; and finally 72° C., 7 minutes. When using the two sets of primers, a prominent amplicon at the expected size of 0.4-kb is observed in an agrose gel. The 0.4-kb DNA fragment is isolated by agarose-gel elution using a Rapid Gel Extraction System (Marligen Biosciences, Ijamsville, Md.). It is then blunt-end ligated into a linearized pT7Blue-3 vector using a Perfectly Blunt Cloning Kit (Novagen, Madison, Wis.) according to the manufacturer's instructions. The recombinant DNA is transfected into competent E. coli DH5α (Invitrogen, Carlsbad, Calif.) using manufacturer's instructions followed by isolation of the amplicon by using Gen-Elute Plasmid Prep Kit (Sigma-Aldrich, St. Louis, Mo.) according to manufacturer's instructions and sequencing of the amplicon on Applied Biosystems 3730 DNA Analyzer (Life Technologies Corp., Carlsbad, Calif.) using manufacturer's instructions. Nucleotide sequencing definitively confirms that a piece of rhlC gene was amplified using the nested PCR protocol. When the same nested PCR protocol is applied to the genomic DNA of P. chlororaphis NRRL B-30761 using the same four nested primers, the specific amplified DNA fragment of the anticipated size of 0.4-kb is not obtained. Nevertheless, nonspecific bands in the region of 0.4 kb are excised, and their nucleotide sequences are determined after subcloning them into E. coli using pT7Blue-3 vector according to the manufacturer's instructions. None of these subcloned amplicons (13 randomly chosen cloned amplicons ranging in size from 0.4- to 0.6-kb) contain nucleotide sequences over their entire length that matched rhlC on BLAST analyses. These results suggest that the lack of $R_2L$ synthesis by P. chlororaphis NRRL B-30761 is likely caused by the absence of rhlC or a gene even slightly homologous to the sequences of found in $R_2L$-producing organisms such as P. aeruginosa.

Example 3 Construction of Recombinant P. chlororaphis Expressing a Heterologous Rhamnosyltransferase C A goal of generating a genetically engineer nonpathogenic P. chlororaphis NRRL B-30761 which is capable of producing $R_2L$ is undertaken by first transfecting and then expressing P. aeruginosa rhlC in P. chlororaphis. Such a transgenic bacterium would be valuable for use in the production of $R_2L$ intended for food and medical applications that are sensitive to the potential occurrence of even a trace amount of pathogenic substance(s) in the product. Using the nested PCR procedure described above in Example 2, $rhlC_{Pae}$ in P. aeruginosa PAO1 is amplified. In the first-round PCR, primers CL-14-134UP (SEQ ID NO: 21) and CL-14-134DOWN (SEQ ID NO: 22) which are designed based on the rhlC and flanking sequences of P. aeruginosa PAO1 genomes (GeneID: 877665) are used. In the second-round, primers RTII-UP (SEQ ID NO: 23) and RTII-DOWN (SEQ ID NO: 24) (see, Rahim, et al. 2001. Molecular Microbiology 40:708-718) are used but with BamHI site built into the 5'-terminus of RTII-UP instead of EcoRI, and HindIII site in RTII-DOWN instead of BamHI. This nested PCR procedure results in the isolation of a 1.2-kb amplicon matching the expected size of the P. aeruginosa rhlC. This amplicon is blunt-ended using Perfectly Blunt cloning kit (Novagen, Billerica, Mass.) per manufacturer's instructions. This 1.2-kb amplicon is spliced into the blunt-end SspI site of a previously described expression vector pBS29-P2-gfp containing a P. syringae P2 promoter (Solaiman and Swingle, 2010. New Biotechnology 27:1-9) which is dephosphorylated using calf intestinal alkaline phosphatase enzyme (Invitrogen, Carlsbad, Calif.) per manufacturer's instructions. The P2 promoter is a constitutive promoter from P. syringae and is active in P. chlororaphis. Two recombinant plasmids, pBS29-P2-$rhlC_{Pae}$ (in which the rhlC is aligned with the promoter P2) and pBS29-P2-inv-$rhlC_{Pae}$ (in which the orientation of rhlC is opposite to promoter P2), are first constructed and transfected in competent E. coli DH5α (Invitrogen, Carlsbad, Calif.). The E. coli are grown and undergo a plasmid miniprep to isolate the pBS29 vector using the Zyppy Plasmid Miniprep Kit (Zymo Research, Irvine Calif.), and the pertinent nucleotide sequences (especially $rhlC_{Pae}$) are verified by sequence determination using Applied Biosystems 3730 DNA Analyzer (Life Technologies, Carlsbad, Calif.). The nucleotide sequence of $rhlC_{Pae}$ is in SEQ ID NO: 25 and the amino acid sequence of $RhlC_{Pae}$ is in SEQ ID NO: 26 (GeneID: 877665). The recombinant plasmids and the vector (i.e., pBS29-P2-gfp as negative control) are then individually electroporated into P. chlororaphis NRRL B-30761 using a previously described protocol (Soliaman, 1998, Biotechnol. Technique 12:829-832) to obtain 3 transformant strains separately containing the vector, the pBS29-P2-$rhlC_{Pae}$, and pBS29-P2-inv-$rhlC_{Pae}$.

It is noted that instead of using pBS29-P2, one could use any expression vector containing an inducible or constitutive promoter that is active in Pseudomonas spp. and which replicates in Pseudomonas spp. Further, the use of tetracycline resistance and kanamycin resistance genes within pBS29-P2 or any other expression vector is not necessary because other selection marker genes are known in the art field and could be used. In addition, one could delete gfp from pBS29-P2 and still have an acceptable plasmid to use for expression of rhlC. Alternatively, rhlC could be stably integrated into the genome of the Pseudomonas spp. using homologous recombination. See, e.g., Casey, et al. 1991 Appl. Environ. Microbiol. 57(9):2677-2682; and Ravatn, et al. 1998 J. Bacteriol. 180(17): 4360-4369.

Example 4 Production and Characterization of $R_2L$ from P. chlororaphis [pBS29-P2-$rhlC_{Pae}$]

The next step is to test the ability of P. chlororaphis [pBS29-P2-$rhlC_{Pae}$] to biosynthesize $R_2L$ in defined medium. Cultures of P. chlororaphis [pBS29-P2-$rhlC_{Pae}$] or the control strain harboring plasmid [pBS29-P2-gfp] are grown in six 1-L Erlenmeyer flasks each containing 200 mL of a Mineral Salts Medium (MSM) containing 2% glucose and 35 µg/mL kanamycin. (See Gunther, et al. 2005 and U.S. Pat. No. 7,202,063.) Cultures are grown in a refrigerator-incubator at 25° C. without shaking. At day 7, the cultures from all six flasks for each organism are pooled and lyophilized until dry. The weight of the dry culture is recorded as the cell-dry-weight yield. The entire dried material (15-20 g, see Table 1) is successively extracted twice with 150 and 75 mL, respectively, of an ethanol/chloroform (1:2 v/v) mixture. The extract is filtered through Whatman No. 2 paper. The solvent of the clarified extract is removed by evaporation using a Buchi Rotovapor R-124 (Brinkmann Instruments; Westbury, N.Y.) until a syrupy material remained in the round-bottom flask. The flask is placed in a desiccator under vacuum for further drying. The weight of the dry syrupy material is recorded as crude rhamnolipid yield.

After lyophilizing the entire culture at the end of fermentation, the dried materials are subject to direct organic solvent-extraction. The solvent is removed by evaporation to obtain crude rhamnolipid preparations, which has a syrupy consistency. The weight of the crude rhamnolipid syrup is recorded as product yield value. Results in Table 2 demonstrate that P. chloraraphis transformant containing pBS29-P2-$rhlC_{Pae}$ produces crude rhamnolipid at a yield of 290 mg/1.2 L of culture, with a total cell-dry-weight yield of 18.3 g (per 1.2 L culture). In comparison, P. chlororaphis [pBS29-P2-gfp] control strain yields 310 mg crude rhamnolipid and 16 g of cell-dry-weight under similar fermentation conditions. No appreciable difference in terms of cell growth and rhamnolipid synthesis is observed between the transformant expressing heterologous rhlC$_{Pae}$ and its control counterpart expressing gfp (Solaiman and Swingle, 2010) (see Table 2).

TABLE 2

Large-scale rhamnolipid yields

| Strain | Cell Dry Weight[a] (g) | Crude rhamnolipid[a] (mg) | Purified R$_1$L (mg) | Purified R$_2$L (mg) |
|---|---|---|---|---|
| P. chlororaphis [pBS29-P2-gfp] | 16.0 | 310 | 93 | n.d.[b] |
| P. chlororaphis [pBS29-P2-rhlC$_{Pae}$] | 18.3 | 750; 290 | 55; 125 | 37; 89 |

[a]Materials were obtained from 1.2 L cultures
[b]No R$_2$L was chromatographically isolatable The total rhamnolipid yields, however, are lower than the values reported previously (Gunther, et al. 2005). Not wishing to be bound to any particular hypothesis, one possible explanation for this yield reduction is that the expression of a heterologous gene (i.e., rhlC in the test strain or gfp in the control sample) is metabolically (e.g., reducing power of NADH and FADH$_2$) and/or energetically (e.g., ATP or other molecules with high-energy bond) demanding, resulting in the diversion of resources from rhamnolipid synthesis. Also, it is possible that the use of an antibiotic (in this case, kanamycin at 35 µg/mL) to ensure plasmid stability negatively affects the overall yields of cell biomass and metabolite (i.e., rhamnolipid) syntheses. Bacterial rhamnolipid synthesis has always been plagued by insufficient yield to achieve commercial viability. A literature survey on this subject generally shows that the reported yields for rhamnolipid production are typically <1 g/L culture under batch-fermentation conditions. (See, Dubey and Juwarkar 2001. *World J. Microbial. Biotechnol.* 17:61-9; and Santa Anna. et al. 2002. *Braz. J. Chem. Eng.* 19:159-66.) For valid comparison, only isolated rhamnolipid yields and not those colorimetrically determined concentrations are considered here. More complex or sophisticated fermentation system, such as the recently reported 4-cycle bioprocess (Heyd, et al, 2011. *Biotechnology Progress* 27:706-716), could in fact lead to an increased production of rhamnolipid resulting in higher product yield. In this method, bacteria are entrapped in magnetic alginate beads. After each cycle of fermentation, the beads are held by magnetic field while the culture broth is drained to harvest the rhamnolipids. Fresh culture broth is replenished, and another cycle of fermentation is performed with the retained immobilized bacteria. It is envisioned that this fermentation method with the *P. chlororaphis* strains described herein could lead to high-yield production of rhamnolipid from nonpathogenic bacterial host.

Example 5 Chromatographic Separation of Rhamnolipid, LC/MS Determination, and Tensiometric Measurement To quantify the relative amounts of R$_2$L and R$_1$L that were produced, one must physically separate and weigh them. While a technique such as LC/MS can in principle provide equivalent information, if the sample is a complicated mixture of many compounds, as these are, baseline separation and integration of peaks may be difficult to achieve. Separation using silica gel chromatography is feasible to perform. The crude material obtained by ethanol/chloroform extraction (see Example 4 above) is dissolved in 90:10 chloroform/methanol and is applied to a column of 50 g silica (Fisher Scientific; Fairlawn, N.J.) that is packed with the same solvent. Elution with this solvent affords a non-polar fraction which is not characterized or identified. Monorhamnolipids, including R$_1$L, are eluted next from the column by adding a more polar solvent mixture of 80/20/1 chloroform/methanol/water (solvent A) to the column. Finally, the dirhamnolipids, being more polar, are challenging to elute, and require a small amount of acetic acid in the elution solvent to remove them from the silica. Thus, 70:30:2:0.4 chloroform/methanol/water/acetic acid (solvent B) is added to the column, which is sufficient to elute both the R$_2$L and an unidentified compound. The fractions containing these two compounds (i.e., R$_2$L and the unknown contaminant) are pooled, dried, and re-applied to a new silica gel column (30 g) packed in solvent A. The unknown contaminant is removed with this solvent, and then the R$_2$L is eluted with solvent B. For R$_1$L and R$_2$L samples, fractions are pooled and dried, then stored under vacuum in a desiccator until constant weight is attained. Two separate preparations from the transformant *P. chlororaphis* [pBS29-P2-rhlC$_{Pae}$] are treated in this manner.

Figure 3A:
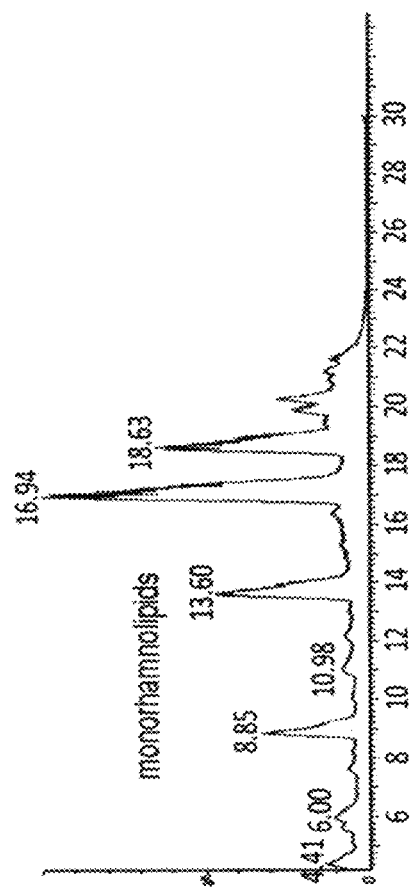
FIG. 3 is a liquid chromatography mass spectroscopy (LC-MS) spectrum of silica column-purified R$_1$L from the control strain *P. chlororaphis* [pBS29-P2-gfp] (top) and R$_2$L from *P. chlororaphis* [pBS29-P2-rhlC$_{Pae}$] (bottom). Letters A-F refer to the compositions of the alkyl chains: A=C8/C10, B=C10/C10, C=C10/C12:1, D=C10/C12:0, E=C12:1/C12:0, F=C12:0/C12:0.
Figure 3B:
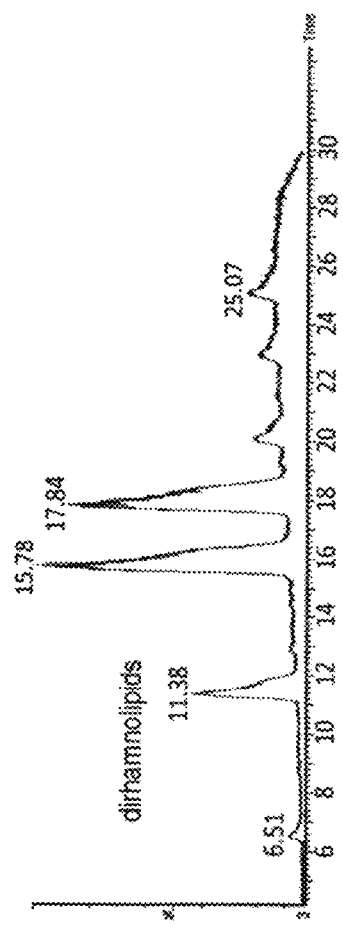

The first crude rhamnolipid preparation yields 125 mg R$_2$L and 55 mg R$_1$L, while the second contains 89 mg R$_2$L and 37 mg R$_2$L. Silica gel purification of the control preparation from *P. chlororaphis* [pBS29-P2-gfp], on the other hand, gives 93 mg R$_1$L, and no R$_2$L is observed. That there should be R$_1$L present in these preparations is unsurprising, because at the time of harvest some R$_1$L will not have been operated on by the RhlC enzyme. The identity of R$_1$L and R$_2$L is verified by LC/MS (see FIG. 3).

Surface tension measurements for R$_1$L and R$_2$L are performed as follows. The purified R$_2$L samples from the two urns described above are redissolved in 1:1 methanol/chloroform, are combined, are dried in vacuo, and are dissolved in 150 mL deionized water to give an approximately 2.1 mM solution. The R$_1$L samples from the two runs above are treated similarly to give an approximately 1.2 mM solution. These molar concentrations are only approximations, because each type of rhamnolipid is present with several different carbon chain lengths. The most abundant molecular weight species is used to calculate concentration, approximately 676 Da for R$_2$L and approximately 510 Da for R$_1$L. Measurements are performed with the standard Wilhelmy plate method (see for example, Talom, et al. 2012. *Journal of Colloid and Interface Science* 387:180-186) on a Data-Physics Instruments GmbH DCAT-11 tensiometer (Filderstadt, Germany) at ambient temperature, 21-22° C. Solutions are filtered through a fine (4.5-5.0 micron) glass fit prior to use.

These measurements demonstrate that the R$_1$L attains slightly lower surface tension than R$_2$L. The minimum surface tension of approximately 26 mN/m is significantly lower than the range of 32-34 mN/m observed for another biosurfactant, sophorolipids (SL), and roughly comparable to that observed for mannosylerythritol lipid (MEL). Neither rhamnolipid is particularly efficient as a surfactant, however, their CMC values (in the range of 0.1 mM) are about an order of magnitude higher than those seen for SL or MEL.

Figure 4A:
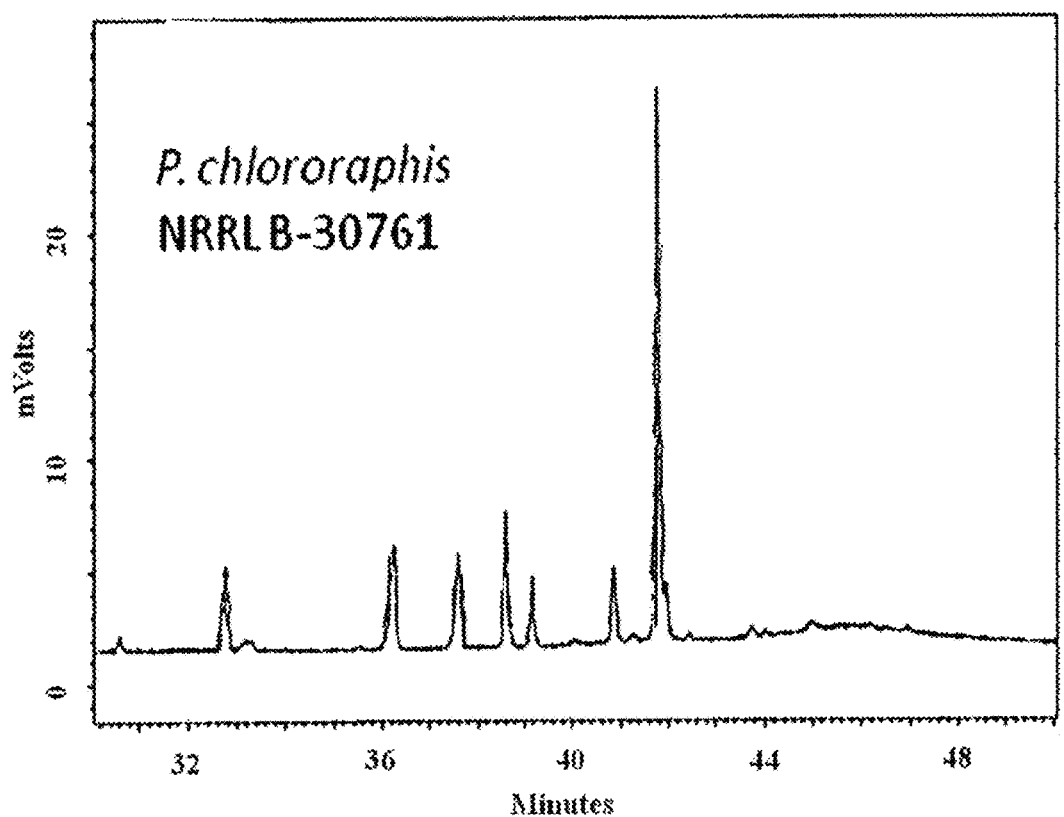
FIG. 4A is a HPLC chromatogram of crude rhamnolipids produced by *P. chlororaphis* NRRL B-30761 under non-stirring conditions.
Figure 4B:
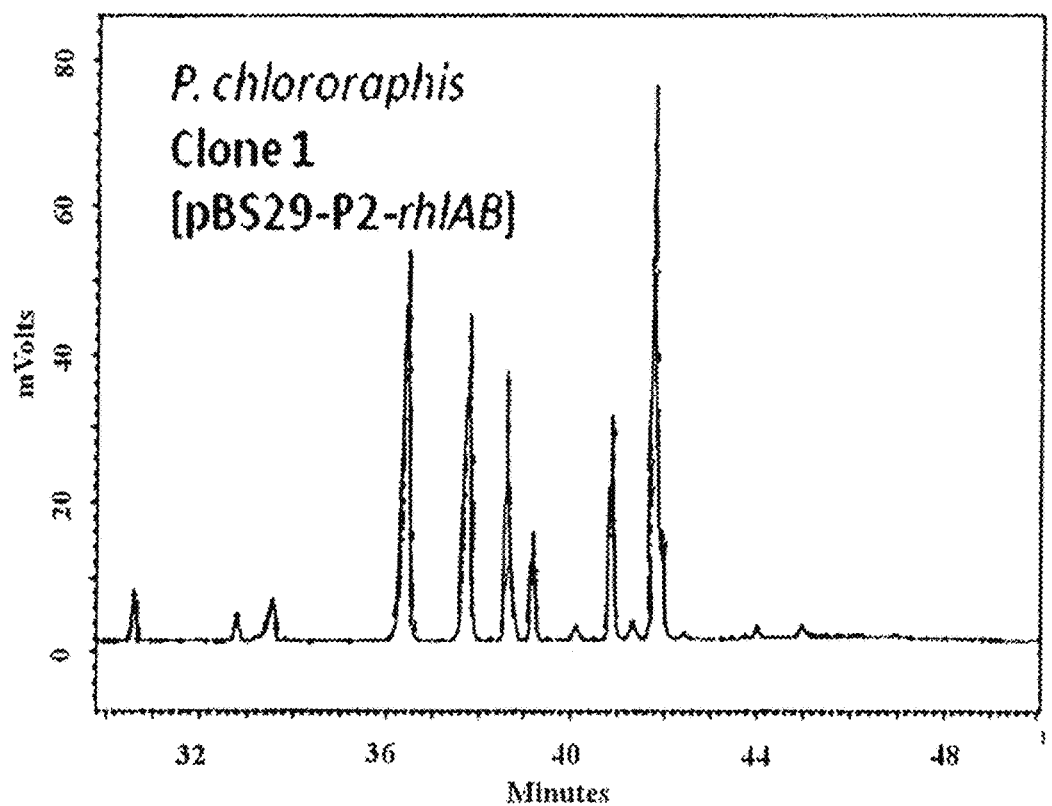
FIG. 4B is a HPLC chromatogram of crude rhamnolipids produced by *P. chlororaphis* [pBS29-P2-rhlAB] clone 1 under non-stirring conditions.
Figure 4C:
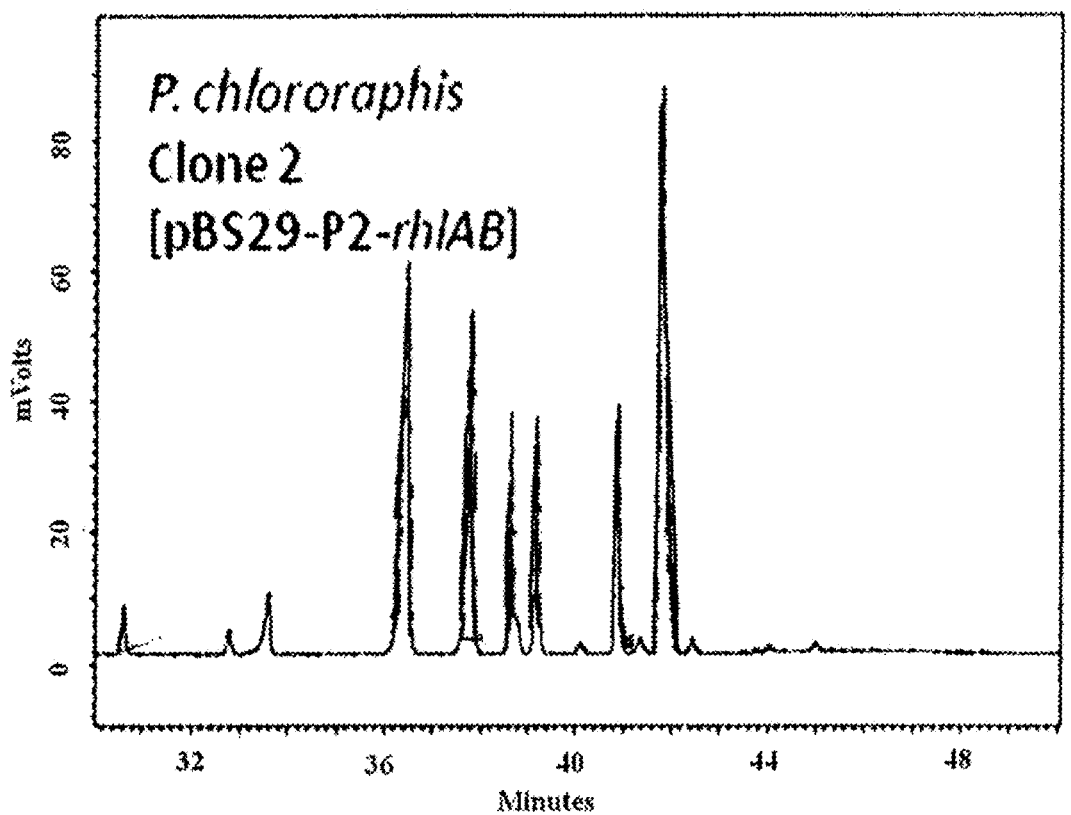
FIG. 4C is a HPLC chromatogram of crude rhamnolipids produced by *P. chlororaphis* [pBS29-P2-rhlAB] clone 2 under non-stirring conditions.
Figure 5:
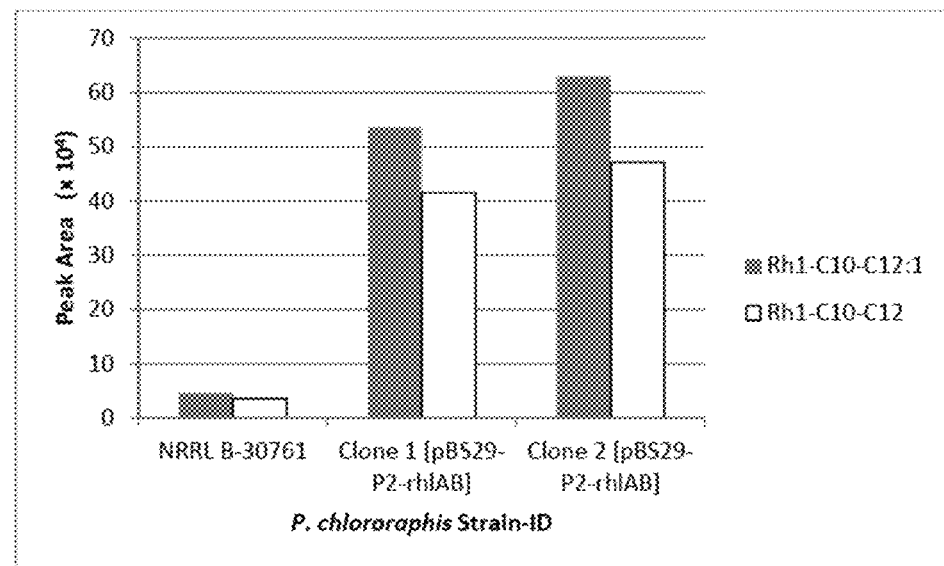
FIG. 5 shows integrated areas of rhamnolipid peaks of *P. chlororaphis* NRRL B-30761 and its pBS29-P2-rhlAB recombinant strains (clones 1 and 2) cultured under non-stirring conditions. Monorhamnolipids (Rh1-C10-C12:1 and Rh1-C10-C12) eluted at retention times of about 36.5 and 37.8 min, respectively.
Figure 6:
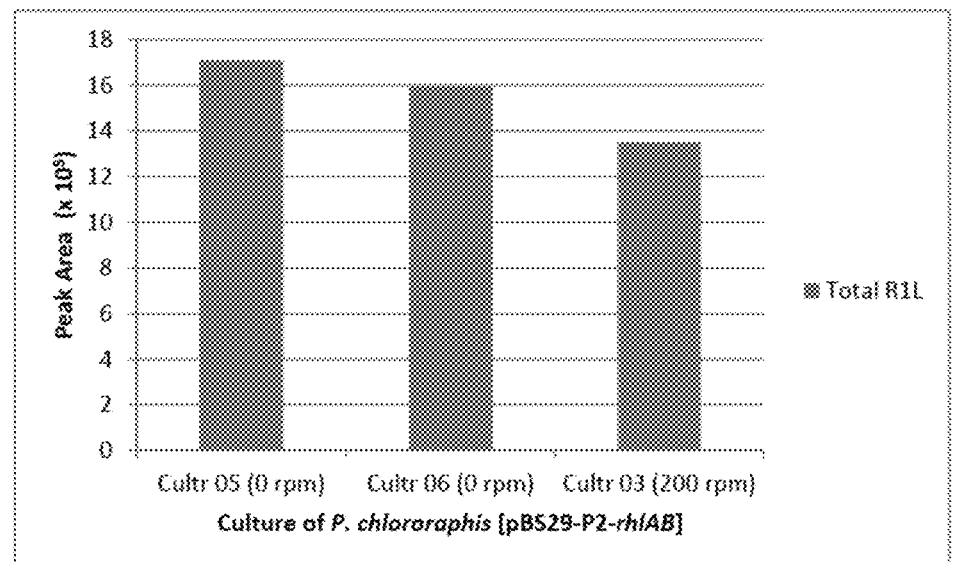
FIG. 6 shows the production of monorhamnolipids by *P. chlororaphis* [pBS29-P2-rhlAB] recombinant strain under static growth and at 200 rpm rotary shaking.

Example 6 Increased R$_1$L and R$_2$L Production Under Stirring Conditions Using rhlA and rhlB To release the expression of rhlA and rhlB in *P. chlororaphis* NRRL B-30761 from the control of oxygen resulted from shaking or stirring of culture, a recombinant expression vector pBS29-P2-rhlAB is constructed in which the contiguous rhlA$_{Pch}$ (SEQ ID NO: 12) and rhlB$_{Pch}$ (SEQ ID NO:

14) genes are placed under the control of (i.e., operably linked to) the constitutive promoter P2 (Solaiman and Swingle, 2010, *New Biotechnol.* 27:1-9). pBS29-P2-rhlAB is then transfected into *P. chlororaphis* NRRL B-30761 by electroporation technique (Solaiman, 1998. *Biotechnol. Techniques* 12:829-932). In this recombinant *P. chlororaphis*, rhlA and rhlB previously in this bacterium remains unchanged. The resultant transformant, *P. chlororaphis* [pBS29-P2-rhlAB], is grown in media as described supra. As shown in FIGS. 4A, 4B, and 4C, and in FIG. 5, the recombinant strains produce, under non-stirring conditions, about 10-fold higher yield of rhamnolipids than the parental *P. chlororaphis* NRRL B-30761 strain. Monorhamnolipids ($Rh_1$-$C_{10}$-$C_{12:1}$ and $Rh_1$-$C_{10}$-$C_{12}$) eluted at retention times of about 36.5 and 37.8 minutes, respectively as seen FIG. 5. FIG. 6 shows that *P. chlororaphis* [pBS29-P2-rhlAB] recombinant strain can produce $R_1L$ at comparable yields regardless of whether or not the culture was shaken at a speed (rotary) of 200 rpm. This 10-fold higher yield of rhamnolipids compared to previously described yields of recombinant *P. chlororaphis* NRRL B-30761 is surprising in light of the complexity of producing rhamnolipids.

To obtain $R_2L$ production in stirring conditions, $rhlC_{Pae}$ is added to the expression vector pBS29-P2-rhlAB and transformed into *P. chlororaphis* NRRL B-30761. This new expression vector, pBS29-P2-rhlABC, contains $rhlA_{Pch}$ (SEQ ID NO:12), $rhlB_{Pch}$ (SEQ ID NO. 14), and $rhlC_{Pae}$ (SEQ ID 25) which are all operationally linked to P2 promoter. To generate this expression vector, the circular pBS29-P2-rhlAB (supra) plasmid is cut with restriction enzyme XbaI located a short distance downstream from the end of rhlB. The thus linearized plasmid with 5'-protuding ends is treated with Klenow DNA polymerase enzyme to render it blunt-ended, then with calf intestinal alkaline phosphatase enzyme to remove the phosphate groups thereby preventing possible self-recircularization. Separately, $rhlC_{Pae}$ is cloned from pBS29-P2-$rhlC_{Pae}$ (supra) by PCR using primers RTII-UP (SEQ ID NO: 23) and RTII-DOWN (SEQ ID NO: 24), and the resultant 1.2-kb amplicon is blunt-ended using Perfectly Blunt cloning kit (Novagen, Billerica, Mass.) per manufacturer's instructions (supra). This $rhlC_{Pae}$ is ligated to the linearized pBS29-P2-rhlAB using T4 DNA ligase enzyme. The resultant circular pBS29-P2-rhlABC is transfected into *P. chlororaphis* NRRL B-30761. Production of $R_2L$ under shaking conditions is verified as described supra.

Example 7 Controlled Production of $R_1L$ and $R_2L$ by *P. chlororaphis*

It would be beneficial to be able to control the production of $R_1L$ and $R_2L$ by *P. chlororaphis* so that one can produce approximately 100% $R_1L$ or approximately 100% $R_2L$ or a desired proportion of $R_1L$ and $R_2L$. The key is to control the expression of rhlC and either rhlA or rhlB or both rhlA and rhlB using inducible promoters (henceforth IP's). Because *P. chlororaphis* lacks rhlC, an expression vector containing $rhlC_{Pae}$ (or rhlC from another bacteria) under control of an inducible promoter is transfected into *P. chlororaphis* so that the bacteria can convert $R_1L$ to $R_2L$. *P. chlororaphis* naturally expresses rhlA and rhlB so one can either delete one or both of rhlA and rhlB from *P. chlororaphis* by site-directed mutagenesis via a cross-over deletion and transfecting the deleted gene (either rhlA or rhlB or both) back into the mutated *P. chlororaphis* via an expression vector containing one or both of these genes under control of (i.e., operably linked to) an inducible promoter distinct from the inducible promoter controlling the expression of rhlC. In this manner, one can prevent the expression of rhlC and produce only or primarily $R_1L$. Then if one wants *P. chlororaphis* to produce $R_2L$, one suppresses the inducible promoter controlling rhlA or rhlB or both rhlA and rhlB, and activates the promoter that controls the expression of rhlC. The amount of time that one activates the inducible promoter controlling rhlC expression influence the ratio of $R_1L$ to $R_2L$. Non-limiting examples of inducible promoters and their activators/repressors include the following:

heat shock promoters induced by heating the cells (U.S. Pat. No. 4,710,473);

lacZ promoter induced by IPTG (isopropyl-β-D-thiogalactopyranoside);

tetracycline promoter (tet) induced by tetracycline (Geissendoefer, et al. 1990. *Appl. Micriobiol. Biotechnol.* 33:657-663);

araS promoter inducible by arabinose (Lubelska, et al. 2006. *Extremophiles* 10(5):383-91);

arabinose-inducible $P_{BAD}$ promoter from *Escherichia coli* (Guzman, et al. 1995. *J. Bacteriol.* 177:4121-4130);

pXyl-xylR promoter induced by xylose (Kim, el ah 1996 *Gene* 181:71-76);

pSpac-lacI using lac operon and IPTG (Yansura, et al. 1984 *Proc. Natl. Acad. Sci. USA* 81:439-443);

alkane-inducible promoter $P_{alkB}$ and alkS (Nieboer, et al. 1993. *Mol. Microbial.* 8:1039-1051);

$P_{ugp}$/phoA phosphate-regulated promoters (Su, et al. 1990. *Gene* 90:129-133;

http://wolfson.huji.ac.il/expression/vector/ Promoters.html#promoters);

cadA regulated by pH and cadR (http://wolfson.huji.ac.il/expression/vector/ Promoters.html#promoters); and rhlR controlled by quorum-sensing and/or biofilm formation (Reis, et al. 2001. *Bioresource Tech.* 102:6377-6384).

Knock-out strains of *P. chlororaphis* NRRL B-30761 are constructed in which rhlA, rhlB, rhlA-rhlB genes are inactivated through a gene-disruption plus homologous recombination mechanism using a method previously described and routinely practiced in this laboratory (see, Solaiman, et al. 2003. *Appl. Microbial. Biotechnol.* 62:536-543). An alternative method for oligo-mediated allelic replacement procedure employs recombinase enzymes (see, Bryan and Swanson 2011. *Mol. Microbiol.* 80:231-247; Swingle, et al. 2010. *Mol. Microbiol.* 75:138-148; Wang, et al. 2009. *Nature*, 460:894-898) to obtain the knock-out strains. Successful construction of rhlA(−), rhlB(−), or rhlA(−)-rhlB(−) knock-out *P. chlororaphis* strains is confirmed by their inability to produce $R_1L$ using production and detection methods described supra. Next, expression vectors are constructed that express rhlA, rhlB, or rhlA-rhlB operably linked to one of the inducible promoters, $IP_1$, described supra or any other suitable inducible promoter. Vector pCN51 (Nieto, et at 1990. *Gene* 87:145-149: Solaiman, et al. 2002. *Current Microbiology* 44:189-195) is used to carry $IP_1$-rhlA, $IP_1$-rhlB, or $IP_1$-rhlA-rhlB into the corresponding *P. chlororaphis* knock-out strains. Successful complementation of the knock-outs is confirmed by production of $R_1L$ upon, and only upon, the addition of the appropriate inducer, $IND_1$. Finally, pBS29-P2-$rhlC_{Pae}$ is transfected into the complemented *P. chlororaphis* knock-outs (i.e., *P. chlororaphis* rhlA(−) [pCN51-$IP_1$-rhlA], *P. chlororaphis* rhlB(−) [pCN51-$IP_1$-rhlB], or *P. chlororaphis* rhlA(−)-rhlB(−) [pCN51-$IP_1$-rhlA-rhlB]). To produce near-exclusively (approximately 100%) the $R_2L$, the recombinant strain *P. chlo-*

*roraphis* rhlA(−) [(pCN51-IP$_1$-rhlA)+(pBS29-P2-rhlC$_{Pae}$)], *P. chlororaphis* rhlB(−) [(pCN51-IP$_1$-rhlB)+(pBS29-P2-rhlC$_{Pae}$)], or *P. chlororaphis* rhlA(−)-rhlB(−) [(pCN51-IP$_1$-rhlA-rhlB)+(pBS29-P2-rhlC$_{Pae}$)] is grown in the presence of the inducer, IND$_1$. Production of R$_1$L occurs, which is then acted on by the gene-product of rhlC to yield R$_2$L. IND$_1$ is then removed resulting in cessation of new R$_1$L synthesis. Existing remaining R$_1$L is then completely converted to R$_2$L by the gene-product of rhlC.

Instead of transfecting the *P. chlororaphis* knock-outs (i.e., *P. chlororaphis* rhlA(−) [pCN51-IP$_1$-rhlA], *P. chlororaphis* rhlB(−) [pCN51-IP$_1$-rhlB], or *P. chlororaphis* rhlA(−)-rhlB(−) [pCN51-IP$_1$-rhlA-rhlB]) with pBS29-P2-rhlC$_{Pae}$ (which uses an constitutive promoter), one can operably link rhlC to a second inducible promoter (IP$_2$) different from the inducible promoter used to control expression of rhlA, rhlB, or rhlA-rhlB (IP$_1$) and which is control by a second inducer (IND$_2$). Then pBS29-IP$_2$-rhlC$_{Pae}$ is transfected into the complemented *P. chlororaphis* knock-outs (i.e., *P. chlororaphis* rhlA(−) [pCN51-IP$_1$-rhlA], *P. chlororaphis* rhlB(−) [pCN51-IP$_1$-rhlB], or *P. chlororaphis* rhlA(−)-rhlB(−) [pCN51-IP$_1$-rhlA-rhlB]) to generate either *P. chlororaphis* rhlA(−) [(pCN51-IP$_1$-rhlA)+(pBS29-IP$_2$-rhlC$_{Pae}$)], *P. chlororaphis* rhlB(−) [(pCN51-IP$_1$-rhlB)+(pBS29-IP$_2$-rhlC$_{Pae}$)], or *P. chlororaphis* rhlA(−)-rhlB(−) [(pCN51-IP$_1$-rhlA-rhlB)+(pBS29-IP$_2$-rhlC$_{Pae}$)], respectively. These recombinant bacteria can be grown as described supra in the presence of IND$_1$ to produce R$_1$L. Then one can acid IND2 to the media which induces expression of rhlC which then converts R$_1$L to R$_2$L. Based on the amount of time IND$_1$ and IND$_2$ are present in the media, one can control the relative percentage of R$_1$L to R$_2$L produced by the recombinant bacteria.

Example 8 Production of R$_1$L and R$_2$L Under Stirring Conditions using Heterologous Regulatory Protein RhlR To determine if one could overcome inability of *P. chlororaphis* NRRL B-30761 and pBS29-P2-rhlC$_{Pae}$ transfected *P. chlororaphis* to produce R$_1$L and R$_2$L, respectively, under stirring conditions, rhlR from another species (i.e., heterologous) *P. chlororaphis* subsp. *aureofaciens* (rhlR$_{P.ch-au}$; GenBank Accession No. AAK73190) is transfected into *P. chlororaphis* NRRL B-30761 or *P. chlororaphis* [pBS29-P2-rhlC$_{Pae}$]. DNA encoding rhlR$_{P.ch-au}$ is obtained from commercial vendor and cloned into pCN51 (Nieto, et al. 1990. *Gene* 87:145-149; Solaiman, et al. 2002. *Current Microbiology* 44:189-195) vector downstream of and operably linked to a constitutive promoter, and the resultant recombinant plasmid pCN51-rhlR$_{P.ch-au}$ is transfected by electroporation technique (Solaiman 1998. *Biotechnol. Techniques* 12:829-932) into *P. chlororaphis* NRRL B-30761 or *P. chlororaphis* [pBS29-P2-rhlC$_{Pae}$]. The new species that produce heterologous regulatory protein RhlR$_{P.ch-au}$ which is not affected by oxygen level (i.e., stirring) can now produce R$_1$L (in the case of *P. chlororaphis* NRRL B-30761 host) or R$_2$L (in the case of *P. chlororaphis* [pBS29-P2-rhlC$_{Pae}$]) under stirring conditions.

It is within the scope of this invention to make expression vectors containing the polynucleotides encoding the genes disclosed herein operably linked to a variety of promoters (constitutive and/or inducible) that are active in various bacteria, fungi, algae, plant cells, insect cells, and mammalian cells. These expression vectors can be used to transform the appropriate cells (depending on the organism for which the promoters are active) to generate recombinant cells which can produce monorhamnose-lipids and/or dirhamnose-lipids as described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim:

1. A recombinant *Pseudomonas chlororaphis* that is derived from *P. chlororaphis* NRRL B-30761, said recombinant *P. chlororaphis* further comprises an expression vector, wherein said expression vector comprises a promoter operably linked to a heterologous polynucleotide encoding a heterologous *Pseudomonas* rhamnosyltransferase C, wherein rhlA and rhlB genes in said recombinant *P. chlororaphis* are operably linked to endogenous promoters.

2. The recombinant *Pseudomonas chlororaphis* of claim 1 wherein said heterologous *Pseudomonas* rhamnosyltransferase C comprises the amino acid sequence of SEQ ID NO: 26.

3. The recombinant *Pseudomonas chlororaphis* of claim 2 wherein said heterologous *Pseudomonas* rhamnosyltransferase C comprises the nucleotide sequence of SEQ ID NO: 25.

4. A method of producing dirhamnose-lipid comprising culturing said recombinant *P. chlororaphis* of claim 1 in medium capable of supporting rhamnose-lipid biosynthesis.

5. The method of claim 4 wherein said heterologous *Pseudomonas* rhamnosyltransferase C comprises the amino acid sequence of SEQ ID NO: 26.

6. The method of claim 5 wherein said heterologous *Pseudomonas* rhamnosyltransferase C comprises the nucleotide sequence of SEQ ID NO: 25.

7. A method for producing dirhamnose-lipid comprising growing said recombinant *Pseudomonas chlororaphis* of claim 1 in medium capable of supporting dirhamnose-lipid biosynthesis.

8. The method of claim 7, wherein said heterologous rhamnosyltransferase C comprises the amino acid sequence of SEQ ID NO: 26.

9. The method of claim 8, wherein said heterologous rhamnosyltransferase C comprises the nucleotide sequence of SEQ ID NO: 25.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gtsaacggcg cgmtggcgac                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gcrttgtcga actgrtcgtg                                              20

<210> SEQ ID NO 3

```
<211> LENGTH: 20
<212> TYPE: DNA
<213> ORGANISM: Artificial Sequence
<220> FEATURE:
<223> OTHER INFORMATION: Primer

<400> SEQUENCE: 3
acsaaggacg acgaggtgga                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
kgctgsgscg gcgcgaacca                                              20

<210> SEQ ID NO 5
<211> LENGTH: 20
<212> TYPE: DNA
<213> ORGANISM: Pseudomonas chlororaphis

<400> SEQUENCE: 5
ccaggcgcaa acgacatcac                                              20

<210> SEQ ID NO 6
<211> LENGTH: 20
<212> TYPE: DNA
<213> ORGANISM: Pseudomonas chlororaphis

<400> SEQUENCE: 6
cccaggacac ggaaaccaag                                              20

<210> SEQ ID NO 7
<211> LENGTH: 20
<212> TYPE: DNA
<213> ORGANISM: Pseudomonas chlororaphis

<400> SEQUENCE: 7
ggcgcttgcc attgactctg                                              20

<210> SEQ ID NO 8
<211> LENGTH: 20
<212> TYPE: DNA
<213> ORGANISM: Pseudomonas chlororaphis

<400> SEQUENCE: 8
caacgcacta cgccacaaac                                              20

<210> SEQ ID NO 9
<211> LENGTH: 21
<212> TYPE: DNA
<213> ORGANISM: Pseudomonas chlororaphis

<400> SEQUENCE: 9
ctggacgatg cgatcacaac g                                            21

<210> SEQ ID NO 10
<211> LENGTH: 22
<212> TYPE: DNA
<213> ORGANISM: Pseudomonas chlororaphis

<400> SEQUENCE: 10
```
ctgcgacgct gcctcttgtg aa 22

<210> SEQ ID NO 11
<211> LENGTH: 297
<212> TYPE: PRT
<213> ORGANISM: Pseudomonas chlororaphis

<400> SEQUENCE: 11

```
Met Ser Arg Ser Gln Tyr Val Ile Lys Lys Ile Phe Lys His Tyr Ser
1               5                   10                  15

Val Ser Val Glu His Ile Gly Asp Ala Pro Asp Arg Lys Asn Val Leu
            20                  25                  30

Leu Val Asn Gly Ala Met Ala Thr Thr Ser Ala Phe Ala Arg Thr Ser
        35                  40                  45

Lys Cys Leu Ala Glu His Phe Asn Val Val Leu Phe Asp Leu Pro Phe
    50                  55                  60

Ala Gly Asn Ser Arg Ala His Asn Pro Asp Arg Cys Leu Val Thr Lys
65                  70                  75                  80

Asp Asp Glu Val Gln Ile Leu Leu Ala Leu Ile Glu Arg Phe Asn Ile
                85                  90                  95

His His Leu Val Ser Val Ser Trp Gly Gly Leu Ser Thr Leu Leu Ala
            100                 105                 110

Leu Ala Lys Asn Pro Asp Ser Val Glu Ser Ser Val Val Met Ser Phe
        115                 120                 125

Ala Pro Gly Leu Asn Ala Pro Met Leu Asp Tyr Val Ser Gly Ala Gln
    130                 135                 140

Ala Leu Val Ala Arg Asp Asn Ala Gly Ile Gly His Leu Leu Asn
145                 150                 155                 160

Gln Thr Leu Gly Lys His Leu Pro Ala Arg Leu Lys Thr Ala Asn Gln
                165                 170                 175

Gln His Met Ala Gln Leu Ile Asn Ala Glu Gln His Gln Ala Arg Phe
            180                 185                 190

His Ile Glu Gln Ala Leu Lys Leu Asn Glu Gly Ala Tyr Leu Pro Gln
        195                 200                 205

Leu Ser Asn Ile Asp Ser His Val His Phe Leu Asn Gly Ala Trp Asp
    210                 215                 220

Glu Tyr Thr Ser Ala Met Asp Val Gln Ser Phe Lys Gln Tyr Ile Arg
225                 230                 235                 240

Asp Cys Ser Phe Ser Ile Ala Gln Ser Ser Gly His Phe Leu Asp Leu
                245                 250                 255

Glu Ser Lys Ala Ala Ala Asn Gly Val His Arg Ala Leu Leu Gly His
            260                 265                 270

Leu Leu Arg Ala Cys Asp Ala Gln Pro Gly Ala Phe Cys Glu Gln Ser
        275                 280                 285

Ala Gln Arg Ala Arg Leu Ser Phe Ala
    290                 295
```

<210> SEQ ID NO 12
<211> LENGTH: 894
<212> TYPE: DNA
<213> ORGANISM: Pseudomonas chlororaphis

<400> SEQUENCE: 12
atgtcgcgta gccaatatgt gatcaagaaa atcttcaagc attattcggt gtcggtggaa    60
cacatcggcg atgcgcctga tagaaagaac gtcctgttgg tcaacggcgc catggccacg   120

```
acgtcggcct tgcccgtac cagtaaatgc ctggccgaac acttcaacgt ggtgctgttt    180
gacttgccgt tcgctggaaa ctcccgcgct cacaaccctg accggtgcct ggtgaccaag    240
gacgacgaag tccagatcct gctggcattg atcgagcgct tcaacattca ccacttggtt    300
tccgtgtcct ggggtggcct gtccaccctg ctggcacttg ccaaaaatcc agacagcgtt    360
gaaagctcag tggtgatgtc gtttgcgcct ggcctcaacg cgccgatgct cgattacgtc    420
agcggggcgc aggcactcgt ggcccgggat gacaacgcag gatcggcca tttgctcaac    480 cagacgctgg gcaagcatct cccggctcga ctcaagaccg ccaatcaaca gcatatggcg    540
cagttgatca cgccgagca gcatcaagcg cgcttccata tcgaacaggc gctcaagctc    600
aatgaagggg cctacttgcc gcaactctcg aacattgaca gtcatgtgca cttcctgaat    660
ggcgcctggg acgaatacac cagcgccatg gacgtgcagt ccttcaagca gtacatccgc    720
gattgcagct ctccattgc ccagagcagc ggacattttc tggacctgga gtccaaggcc    780
gcggccaacg gcgtgcaccg cgcgttgctc gggcatttgc tgagggcatg cgatgcccag    840 ccagggggcgt tttgcgagca gtcggctcaa cgagcgcggc tgagctttgc ctaa          894
```

<210> SEQ ID NO 13
<211> LENGTH: 424
<212> TYPE: PRT
<213> ORGANISM: Pseudomonas chlororaphis

<400> SEQUENCE: 13

```
Met Met Arg Val Ile Met Val Ala Ile Gly Ser Ala Gly Asp Val Phe
1               5                   10                  15

Pro Phe Ile Gly Leu Gly Ala Ala Leu Thr Val Arg Gly His Gln Val
                20                  25                  30

Thr Leu Cys Ser Met Pro Thr Phe Gln Arg Ala Ile Glu Ala Gln Gly
            35                  40                  45

Leu Asn Phe Val Pro Leu Cys Asp Glu Ala Thr Tyr Ser Ala Ala Met
        50                  55                  60

Gly Asp Pro Leu Leu Trp Asp Pro Lys Thr Ser Phe Ala Val Leu Trp
65                  70                  75                  80

Gln Ala Ile Ala Gly Leu Leu Glu Pro Val Tyr Asp Tyr Val Thr Thr
                85                  90                  95

His Asn Thr Asp Asp Thr Val Val Gly Ser Leu Trp Ala Leu Gly
            100                 105                 110

Ala Arg Ile Ala His Glu Lys Tyr Gly Ile Pro Tyr Leu Ser Val Gln
        115                 120                 125

Val Ser Pro Ser Thr Leu Leu Ser Ala His Leu Pro Pro Val His Pro
    130                 135                 140

Thr Phe Asn Val Ser Arg Arg Leu Pro Leu Thr Leu Arg Lys Leu Leu
145                 150                 155                 160

Trp Arg Gly Ile Glu Tyr Leu Ser Leu Asp Arg Thr Cys Ala Pro Gln
                165                 170                 175

Ile Asn Ala Leu Arg His Lys His Gly Leu Pro Gly Val Val Lys Asn
            180                 185                 190

Ile Phe Ser Gln Trp Met His Ala Pro Gln Gly Val Ile Cys Leu Phe
        195                 200                 205

Pro Glu Trp Phe Ala Pro Ala Gln Lys Asp Trp Pro Gln Pro Leu His
    210                 215                 220

Met Ala Gly Phe Pro Leu Phe Asp Gly Gly Ala Pro Gly Leu Asp Glu
225                 230                 235                 240
```

Pro Thr Arg Ala Phe Leu Val Ala Gly Ala Pro Ile Val Phe Thr
            245                 250                 255

Gln Gly Ser Thr Glu His Phe Asp Gln Gln Phe Tyr Arg Phe Ala Leu
        260                 265                 270

Ala Ala Leu His Arg Val Gly Ala Arg Gly Ile Phe Leu Thr Gly Asp
        275                 280                 285

Arg Pro Leu Phe Thr Asp Leu Pro Pro Thr Val Ile Gln Arg Pro Phe
    290                 295                 300

Leu Pro Met Ser Ser Leu Leu Pro His Ala Ala Gly Leu Val His Pro
305                 310                 315                 320

Gly Gly Ile Gly Ala Met Ser Gln Ala Leu Ala Gly Ile Ala Gln
            325                 330                 335

Ile Val Leu Pro Ile Ala His Asp Gln Phe Asp Asn Ala Glu Arg Leu
            340                 345                 350

Val Arg Met Gly Cys Gly Ile Arg Leu Ala Leu Pro Leu Asn Lys Gln
        355                 360                 365

Asp Leu Asp Asp Ala Ile Thr Thr Leu Leu His Asp Ser Arg Leu Gln
    370                 375                 380

Thr Ala Cys Arg Arg Ala Ser Ser Leu Met Pro Cys Asp Ala Ala Ser
385                 390                 395                 400

Cys Glu Thr Ala Val Asn Ala Ile Glu Gln Cys Leu Ala Arg His Ser
            405                 410                 415

Met Pro Arg Leu Arg Gln Ala Ser
            420

<210> SEQ ID NO 14
<211> LENGTH: 1275
<212> TYPE: DNA
<213> ORGANISM: Pseudomonas chlororaphis

<400> SEQUENCE: 14

```
atgatgcgag taatcatggt tgccatcggc tcggccggtg acgttttttcc ctttatcggc     60 ctggggctg ccctgactgt gcgcggtcat caggtcacct tgtgcagcat gccgacgttt     120
cagcgcgcca ttgaggcgca ggggctgaac ttcgtgccgt tatgcgatga ggcgacctac    180
agcgccgcca tgggcgatcc cctattgtgg gacccgaaga cctcattcgc cgtattgtgg    240
caagccatcg ccggcctgct ggaacccgtc tacgactatg taaccactca caataccgac    300
gatacggtgg ttgtcggctc actatgggcc ttggggcac gtatcgccca tgaaaaatac    360
ggcatccctt atctgtccgt ccaagtgtcg ccatccacgt tgctttctgc acatttgccg    420
cccgtgcacc ccaccttcaa tgtgtcgcgg cgcttgccat tgactctgcg caagctgctc    480
tggcgcggga tcgaatacct gagcctggac cgtacctgtg ctccccaaat caacgcacta    540
cgccacaaac atgggctacc aggcgtggtg aagaacatct tcagtcaatg gatgcatgcg    600
ccccaagggg tgatatgcct gttccccgaa tggttcgccc cgcacagaa agactggcca    660 cagccttgc acatggccgg ttttccctct gtcgacggtg gcgcccctgg gctcgatgag    720
cccacacgag cctttctggt tgccggagcg cccctattg tcttcactca aggctccact    780
gagcactttg accagcagtt tatcgtttc gccctggcag cgctgcacag ggtcggtgcc    840
cgcggcattt ttctgaccgg tgatcgaccg ctcttcacgg acctgccgcc caccgtgata    900
cagcgcccgt ttttgccgat gagttcgctg ttgcccacg cggccggtct ggtccacccc    960
ggcggcattg cgccatgag ccaggcgctg gcggccggca ttgcgcagat tgtgctgcct   1020
```

-continued

```
atcgctcatg accagttcga taacgccgaa cgcctggtgc gcatgggatg cggcatacgc    1080
cttgccctac cgttaaacaa acaggacctg gacgatgcga tcacaacgct cttgcacgac    1140
agccggctgc aaacggcctg tcgtcgagcg agcagcctga tgccctgcga cgctgcctct    1200
tgtgaaacag cggtcaacgc cattgagcag tgcctcgcgc ggcattcaat gcctcgcctg    1260
cgccaggcct cataa                                                    1275
```

```
<210> SEQ ID NO 15
<211> LENGTH: 239
<212> TYPE: PRT
<213> ORGANISM: Pseudomonas chlororaphis

<400> SEQUENCE: 15

Met Glu Lys Glu Asn Asp Leu Ile Arg Trp Trp Asp Cys Leu Arg Ile
1               5                   10                  15

Glu Met Cys Lys Gln Gln Asp Glu Thr Gln Val Leu Ala Leu Leu Glu
                20                  25                  30

Arg Glu Val Leu Gln Leu Gly Phe Glu Tyr Tyr Ala Tyr Gly Val Arg
            35                  40                  45

His Leu Thr Pro Phe Thr Arg Pro Arg Thr Glu Ile Cys Gly Ser Tyr
        50                  55                  60

Pro Ala Ser Trp Leu Ala Tyr Glu Lys Gln Asn Tyr Ala Val Asp Pro
65                  70                  75                  80

Ser Ile Leu Ser Gly Leu Arg Ser Thr Glu Met Val Val Trp Asn Asp
                85                  90                  95

Ala Leu Phe Asp Asn Ser Arg Thr Leu Trp Gln Glu Ala Arg Asp Trp
            100                 105                 110

Gly Leu Cys Ile Gly Ala Thr Leu Pro Leu Arg Ser His Asp Arg Ser
        115                 120                 125

Leu Arg Val Leu Ser Val Ala Arg Arg Gln Asp Ile Ile Ser Gln Ala
130                 135                 140

Glu Asn Asn Glu Ile Gln Val Arg Leu Arg Cys Ile Leu Glu Arg Val
145                 150                 155                 160

Thr Leu Arg Leu Thr Asp Leu Gly Asp Ser Glu Arg Ala His Gln Ser
                165                 170                 175

Val Cys Leu Ser Arg Arg Glu Arg Glu Ile Leu Gln Trp Thr Ala Asp
            180                 185                 190

Gly Lys Ser Ser Gly Glu Ile Ala Leu Ile Leu Asn Ile Ser Val Asn
        195                 200                 205

Thr Val Asn Phe His Leu Lys Ala Ile Gln Lys Phe Gly Ala Gly
    210                 215                 220

Asn Lys Thr Leu Ala Ala Ala Tyr Ala Ala Ala Gln Gly Leu Ile
225                 230                 235
```

```
<210> SEQ ID NO 16
<211> LENGTH: 726
<212> TYPE: DNA
<213> ORGANISM: Pseudomonas chlororaphis

<400> SEQUENCE: 16
atggagaagg aaaacgacct cattcgttgg tgggattgct tacgcatcga gatgtgcaag     60
caacaggatg agactcaagt gttagcgctt ctggagcgtg aagtgttgca actggggttc    120
gagtactacg cctatggcgt acgtcacctg acccctttta cacgcccag aaccgagata    180 tgcgggtcct acccgcaag ctggctggca caytacgaga agcaaaacta cgcggstgtc    240
```

```
gatccgtcaa tccttagtgg cttgcgctct accgagatgg tggtatggaa cgacgcactg      300
tttgataaca gccgcacgct gtggcaggaa gctcgggact ggggcttgtg catcggcgcc      360
acactgccgc ttcgaagcca cgaccgttca ctgcgggtac tgtccgtggc tcggcgccaa      420
gacattattt cgcaggctga aaacaatgag attcaagtgc gcctgcgctg catccttgaa      480
cgggtgacac tgcgcctgac agacctgggt gatagcgaac gcgcccacca atcggtctgc      540
ctgagccggc gtgagcggga gatcctgcag tggaccgccg acggcaagag ttcaggagaa      600
attgcgctga tcctcaatat ttccgtcaac accgtaaact ttcacctcaa agccattcag      660
aagaaattcg gcgctggcaa caaaacactg gcggcagcct acgccgctgc acagggcctt      720
atctag                                                                726
```

```
<210> SEQ ID NO 17
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 17
cggcaaccgg cagggnrtng cngg                                             24

<210> SEQ ID NO 18
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t

<400> SEQUENCE: 18
catgccgttc cgggcnmvrt arta                                             24

<210> SEQ ID NO 19
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n is a, c, g, or t

<400> SEQUENCE: 19
cgccggcgcc twyaaysmng g                                                21

<210> SEQ ID NO 20
<211> LENGTH: 24
<212> TYPE: DNA
<213> ORGANISM: Artificial Sequence
```

<220> FEATURE:
<223> OTHER INFORMATION: Primer
<220> FEATURE:
<221> NAME/KEY: misc_feature
<222> LOCATION: (23)..(23)
<223> OTHER INFORMATION: n is a, c, g, or t

<400> SEQUENCE: 20
gccgcagcca gccrtgrtkc atng                                    24

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ctgatgagcg gcctgttcca ctg                                     23

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
catggcgtgc gcgaatggaa gcagaac                                 27

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
gcaggatcca cctacgggag aagaacga                                28

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
cgcaagcttg gcgattcgtt ctacttc                                 27

<210> SEQ ID NO 25
<211> LENGTH: 978
<212> TYPE: DNA
<213> ORGANISM: Pseudomonas aeruginosa

<400> SEQUENCE: 25
atggaccgga tagacatggg cgtgctggtg gtactgttca atcctggcga cgacgacctg        60
gaacaccttg gcgaactggc ggcggcgttt ccgcaactgc gcttccttgc cgtcgacaac       120
tcaccgcaca gcgatccgca gcgcaatgcc cggctgcgcg ggcaaggcat cgccgtgctg       180
caccacggca accggcaggg catcgccggc gccttcaacc agggactcga cgcgctattc       240
cggcgtggcg tgcagggtgt gctgctgctc gaccaggact cccgtcccgg cggcgccttc       300
ctcgccgccc agtggcgcaa cctgcaggcg cgcaacggtc aggcctgcct gctcggccca       360

-continued

```
cggatcttcg accggggtga ccggcgcttc ctgccggcca tccatctcga cggactgacg    420
ctcaggcaat tgtctctgga cggcctgacg accccgcagc gcacctcgtt cctgatctcc    480
tccggctgcc tgctgacccg cgaggcctac cagcgcctcg gccacttcga cgaggaactg    540
ttcatcgacc acgtggacac cgaatacagc ctgcgcgccc aggcgctgga cgtgcccctg    600
tacgtcgacc cgcggctggt cctcgagcac cgcatcggca cgcgcaagac ccgccgcctc    660
ggcggtctca gcctcagcgc gatgaaccac gccccgctgc gccgctacta cctgcgcgc     720 aacggcctgc tggtcctgcg ccgctacgcc cggtcctcgc cgctggccct gctggcgaac    780
ctgccgaccc tgacccaggg cctcgcggtg ctcctgctcg aacgcgacaa gctgctcaag    840
ctgcgctgcc tgggctgggg cctgtgggac ggcctgcggg acgcggcgg cgcgctggag     900 accaaccgcc cgcgcctgct gaagcgcctc gccggcccgg ccgtggcgtc cgtagcttcc    960
ggcaaggcca aggcctag                                                  978
```

<210> SEQ ID NO 26
<211> LENGTH: 325
<212> TYPE: PRT
<213> ORGANISM: Pseudomonas aeruginosa

<400> SEQUENCE: 26

```
Met Asp Arg Ile Asp Met Gly Val Leu Val Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu His His Gly Asn
        50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Thr Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
    210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
```

-continued

```
                260                 265                 270
Leu Glu Arg Asp Lys Leu Leu Lys Leu Arg Cys Leu Gly Trp Gly Leu
            275                 280                 285

Trp Asp Gly Leu Arg Gly Arg Gly Gly Ala Leu Glu Thr Asn Arg Pro
            290                 295                 300

Arg Leu Leu Lys Arg Leu Ala Gly Pro Ala Val Ala Ser Val Ala Ser
305                 310                 315                 320

Gly Lys Ala Lys Ala
                325
```